United States Patent
Shani et al.

(10) Patent No.: US 9,730,393 B2
(45) Date of Patent: Aug. 15, 2017

(54) MICROENVIRONMENT FOR EFFICIENT UPTAKE OF FERTILIZERS AND OTHER AGROCHEMICALS IN SOIL

(71) Applicants: Uri Shani, Ness-Ziona (IL); Asher Vitner, Jerusalem (IL); Matti Ben-Moshe, Reut (IL); Eran Segal, Kibbutz Hulda (IL); Zvi Miller, Kiryat Tivon (IL)

(72) Inventors: Uri Shani, Ness-Ziona (IL); Asher Vitner, Jerusalem (IL); Matti Ben-Moshe, Reut (IL); Eran Segal, Kibbutz Hulda (IL); Zvi Miller, Kiryat Tivon (IL)

(73) Assignee: ADAMA MAKHTESHIM LTD., Airport (IL)

( * ) Notice: Subject to any disclaimer, the term of this patent is extended or adjusted under 35 U.S.C. 154(b) by 0 days.

(21) Appl. No.: 14/214,141

(22) Filed: Mar. 14, 2014

(65) Prior Publication Data
US 2014/0259906 A1    Sep. 18, 2014

Related U.S. Application Data

(60) Provisional application No. 61/793,697, filed on Mar. 15, 2013.

(51) Int. Cl.
*C05G 3/00* (2006.01)
*A01N 25/26* (2006.01)
(Continued)

(52) U.S. Cl.
CPC ............. *A01G 1/001* (2013.01); *A01N 25/04* (2013.01); *A01N 25/26* (2013.01); *C05G 3/0029* (2013.01); *C05G 3/04* (2013.01)

(58) Field of Classification Search
None
See application file for complete search history.

(56) References Cited

U.S. PATENT DOCUMENTS 4,891,223 A * 1/1990 Ambegaonkar ....... A01N 25/26
                                                      424/408
5,187,011 A * 2/1993 Manalastas et al. ..... 428/402.24
(Continued)

FOREIGN PATENT DOCUMENTS

EP    0 605 721    7/1994
EP    0628527    12/1994
(Continued)

OTHER PUBLICATIONS

Webster's New Collegiate Dictionary, 1979 by G. & C. Merriam Co, p. 1354.*

(Continued)

*Primary Examiner* — Wayne Langel
(74) *Attorney, Agent, or Firm* — Gary J. Gershik; Cooper & Dunham LLP

(57) ABSTRACT

The present invention provides a bead comprising: i) an external zone comprising a super absorbent polymer (SAP) that is capable of absorbing at least about 5 times its weight in water, surrounding ii) at least one internal zone comprising a core that contains at least one agrochemical, wherein the external zone is permeable to oxygen when hydrated, or the internal zone is formulated to release the at least one agrochemical into the external zone over a period of at least about one week when the hydrogel of the external zone is hydrated. The present invention also provides methods of using beads of the invention.

20 Claims, 13 Drawing Sheets

(51) Int. Cl.
   *A01G 1/00* (2006.01)
   *C05G 3/04* (2006.01)
   *A01N 25/04* (2006.01)

(56) References Cited

U.S. PATENT DOCUMENTS

| | | | |
|---|---|---|---|
| 5,192,615 A * | 3/1993 | McDougall et al. | .... 428/402.24 |
| 5,204,183 A * | 4/1993 | McDougall et al. | .... 428/402.24 |
| 5,701,699 A | 12/1997 | Carlson et al. | |
| 8,296,996 B2 | 10/2012 | Johnson | |
| 2002/0034550 A1 | 3/2002 | Quong et al. | |
| 2002/0134013 A1* | 9/2002 | Obonai et al. | ................ 47/65.5 |
| 2005/0159315 A1 | 7/2005 | Doane et al. | |
| 2007/0167327 A1 | 7/2007 | Savich et al. | |
| 2009/0163365 A1 | 6/2009 | Bentlage et al. | |
| 2011/0065582 A1 | 3/2011 | Undabeytia Lopez et al. | |
| 2011/0275520 A1* | 11/2011 | Frey et al. | .................. 504/360 |
| 2011/0308154 A1 | 12/2011 | Akay et al. | |
| 2013/0019813 A1* | 1/2013 | Rubin et al. | ................ 119/712 |
| 2014/0024526 A1 | 1/2014 | Jackson et al. | |
| 2014/0227366 A1 | 8/2014 | Zindel et al. | |

FOREIGN PATENT DOCUMENTS

| | | |
|---|---|---|
| WO | WO 96/27573 | 9/1996 |
| WO | WO 98/12154 | 3/1998 |
| WO | WO 2009/023203 | 2/2009 |
| WO | WO 2012/156304 | 11/2012 |
| WO | WO 2012/162840 | 12/2012 |
| WO | WO 2013/158316 | 10/2013 |
| WO | WO 2014/140918 | 9/2014 |

OTHER PUBLICATIONS

Notification of Transmittal of the International Search Report and Written Opinion of the International Searching Authority, or the Declaration, including the International Search Report and Written Opinion of the International Searching Authority, issued Nov. 11, 2014 in connection with PCT International Application No. PCT/IB2014/001194.
Davidson, Drew et al., Materials for Sustained and Controlled Release of Nutrients and Molecules to Support Plant Growth J. of Agricultural and Food Chemistry. vol. 60(4), (2012), pp. 870-876.
Puoci, Francesco et al. "Polymer in Agriculture: a Review." American Journal of Agriculture and Biological Sciences, vol. 3(1): pp. 299-314(2008).
Bashan, Y. et al., "Alginate microbeads as inoculant carriers for plant growth-promoting bacteria," Biol. Fertil. Soils (2002) 35:359-368.
Gonzalez, L. and Bashan, Y., "Increased Growth of the Microalga Chlorella vulgaris when Coimmobilized and Cocultured in Alginate Beads with the Plant-Growth-Promoting Bacterium Azospirillum brasilense," Applied and Mirocenvironmental Microbiology, vol. 66, No. 4, pp. 1527-1531 (2000).
Mallepally, R. et al, "Superabsorbent Alginate Aerogels,".
Shaviv, A. & Mikkelsen, R.L., "Controlled-release fertilizers to increase efficiency of nutrient use and minimize environmental degradation—a review," Fertilizer Research vol. 35, pp. 1-12 (1993).
PCT International Search Report issued Nov. 11, 2014 in connection with PCT International Application No. PCT/IB2014/001194.
Written Opinion of the International Searching Authority issued Nov. 11, 2014 in connection with PCT International Application No. PCT/IB2014/001194.
PCT International Preliminary Report on Patentability issued Sep. 15, 2015 in connection with PCT International Application No. PCT/IB2014/001194, filed Sep. 15, 2015.
PCT International Search Report issued Jan. 13, 2016 in connection with PCT International Application No. PCT/IB2015/001591.
Written Opinion of the International Searching Authority issued Jan. 13, 2016 in connection with PCT International Application No. PCT/IB2015/001591.
Sep. 15, 2015 Cuban Office Action issued in connection with Cuban Patent Application No. 2015-0127.
Mar. 3, 2016 Response to Sep. 15, 2015 Official Action issued by the Cuban Patent Office in connection with Cuban Patent Application No. 2015-0127.
Dec. 30, 2015 Formal Examination issued by the Colombian Patent Office in connection with Colombian Patent Application No. 15-243484.
Mar. 1, 2016 Response to Dec. 30, 2015 Formal Examination in connection with Colombian Patent Application No. 15-243484.
Jan. 13, 2016 Office Action issued by the Ukrainian Patent Office in connection with Ukrainian Patent Application No. a 2015 09767.
Mar. 10, 2016 Response to Jan. 13, 2016 Office Action issued by the Ukrainian Patent Office in connection with Ukrainian Patent Application No. a 2015 09767.
Hopkins, H.T., "Growth and Nutrient Accumulation as Controlled by Oxygen Supply to Plant Roots," *Plant Physiology*, 25(2): 193-209 (1950).
Nicholson, S.E. and Farrar, T.J., "The Influence of Soil Type on the Relationships Between NDVI, rainfall, and soil moisture in semi-arid Botswana I. NDVI Response to Rainfall," *Remote Sensing of Environment*, vol. 50, Issue 2, pp. 107-120 (1994).
Drew M.C., "Oxygen Deficiency and Root Metabolism: Injury and Acclimation Under Hypoxia and Anoxia," *Annual Review of Plant Pnysiology and Plant Molecular Biology*, vol. 48, pp. 223-250 (1997) (abstract only).
Habarurema and Steiner, "Soil Suitability Classification by Farmers in Southern Rwanda," *Geoderna*, vol. 75, Issues 1-2, pp. 79-67 (1997)(abstract only).
Guo, Mingyu, Mingzhu, Rui Liang, and Aizhen Niu, "Granular Ureaformaldehyde Slow-Release Fertilizer with Superabsorbent and Moisture Preservation," *Journal of Applied Polymer Science J. Appl. Polym. Sci.* 99.6, pp. 3230-3235, (2006).
Mikkelsen, R.L. (1995). "Using hydrophilic polymers to improve uptake of manganese fertilizers by soybeans." Fertilizer Research, 41:87-92.

\* cited by examiner

| Requirements | | Tests |
|---|---|---|
| 1. Sustains three dimensional geometry | ⇧ | 1. optimization of hydrated dimensions (up to 5 cm). |
| 2. Root growth into hydrogel and stay in its vicinity. | ⇧ | 2. Monitoring roots grow towards shell with/without nutrients. |
| 3. Maintain original chemical properties & supply agrochemicals at predetermined rate. | ⇧ | 3. Measuring temporal changes in shell conditions – pH, EC, N, P, K, else. |
| 4. Biodegradable | ⇧ | 4. Install to an orchard/plantation |

Figure 12

MICROENVIRONMENT FOR EFFICIENT UPTAKE OF FERTILIZERS AND OTHER AGROCHEMICALS IN SOIL

This application claims the benefit of U.S. Provisional Application No. 61/793,697, filed Mar. 15, 2013, the contents of which is hereby incorporated by reference in its entirety.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF INVENTION

Current practices and technologies yield poor agrochemical use efficiency by plants due to over application (up to 50%) (Shaviv and Mikkelsen 1993). Excessive application of agrochemicals has adverse effects on the environment and is costly for farmers (Shaviv and Mikkelsen 1993). Additionally, many soils and climates are not suitable for growing desired plants such as crops (Habarurema and Steiner, 1997; Nicholson and Farrar, 1994).

New practices and technologies are needed for efficiently improving plant growth.

SUMMARY OF THE INVENTION

The present invention provides a bead comprising:
i) an external zone comprising a super absorbent polymer (SAP) that is capable of absorbing at least about 5 times its weight in water, surrounding
ii) at least one internal zone comprising a core that contains at least one agrochemical,
wherein the external zone is permeable to oxygen when hydrated, or the internal zone is formulated to release the at least one agrochemical into the external zone over a period of at least about one week when the hydrogel of the external zone is hydrated.

The present invention provides a method of growing a plant, comprising adding at least one bead of the invention to the medium in which the plant is grown.

The present invention provides a method of growing a plant, comprising adding multiple beads of the invention to the medium of the plant, wherein the multiple beads comprise three fertilizer compounds, such that the total N, P, and K content as $(NH_4)_2SO_2$, $NH_4H_2PO_4$, and KCl in the medium as part of the beads is about 25, 5, and 30 $g/m^2$, respectively.

The present invention provides a method of generating an artificial zone with predetermined chemical properties within the root zone of a plant, comprising:
i) adding at least two different beads to the root zone of the plant; or
ii) adding at least two different beads to the anticipated root zone of the medium in which the plant, is anticipated to grow,
wherein at least one of the at least two different beads is a bead of an embodiment of the invention.

BRIEF DESCRIPTION OF THE DRAWING

FIG. 12. Tests for bead requirements.

DETAILED DESCRIPTION OF THE INVENTION

Figure 1:
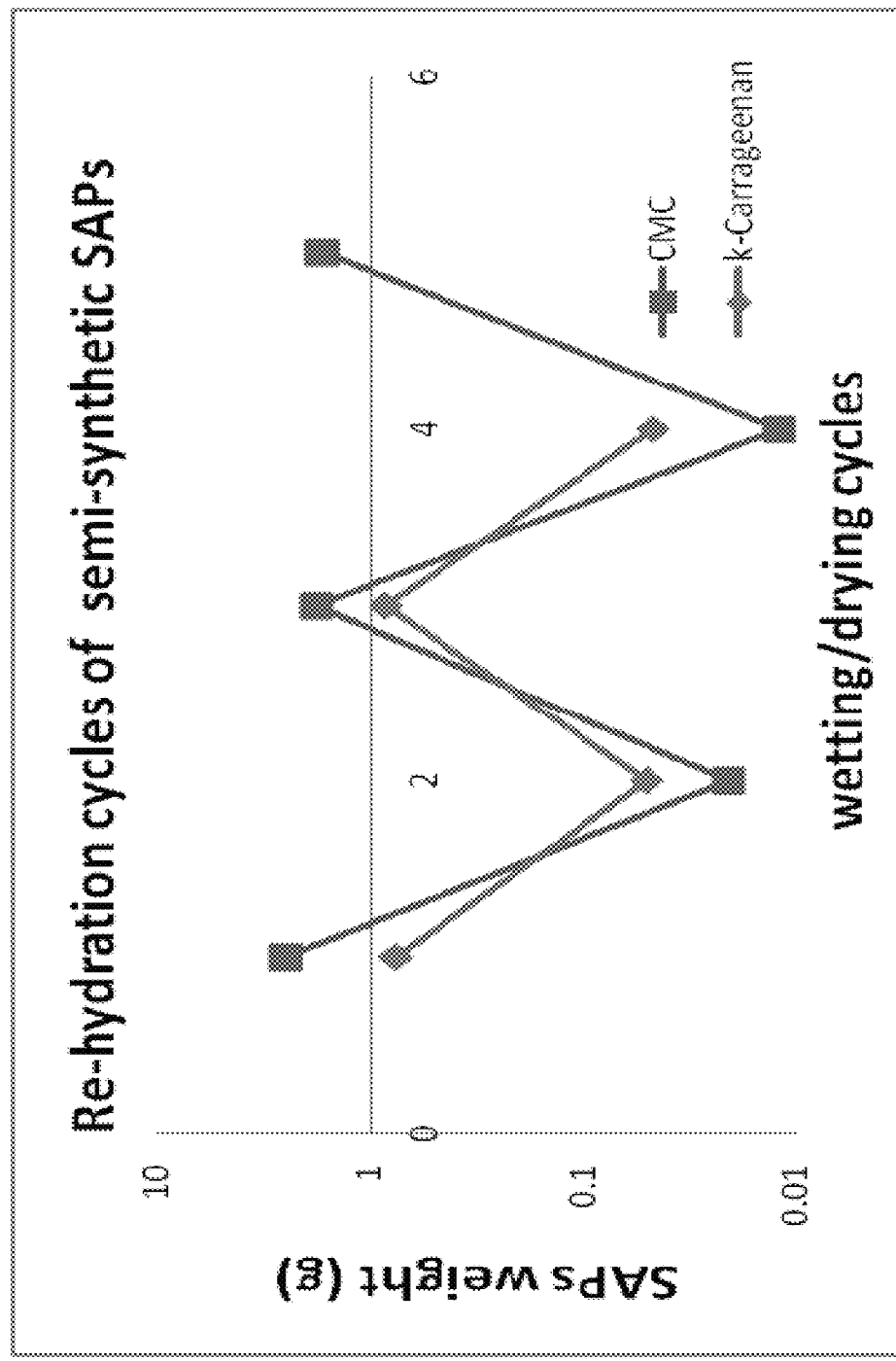
FIG. 1. Swelling behavior of semisynthetic hydrated SAPS following hydration and rehydration cycles in water, FIG. 2. Swelling behavior of hydrated SAPS following hydration and rehydration cycles in soils.
Figure 2:
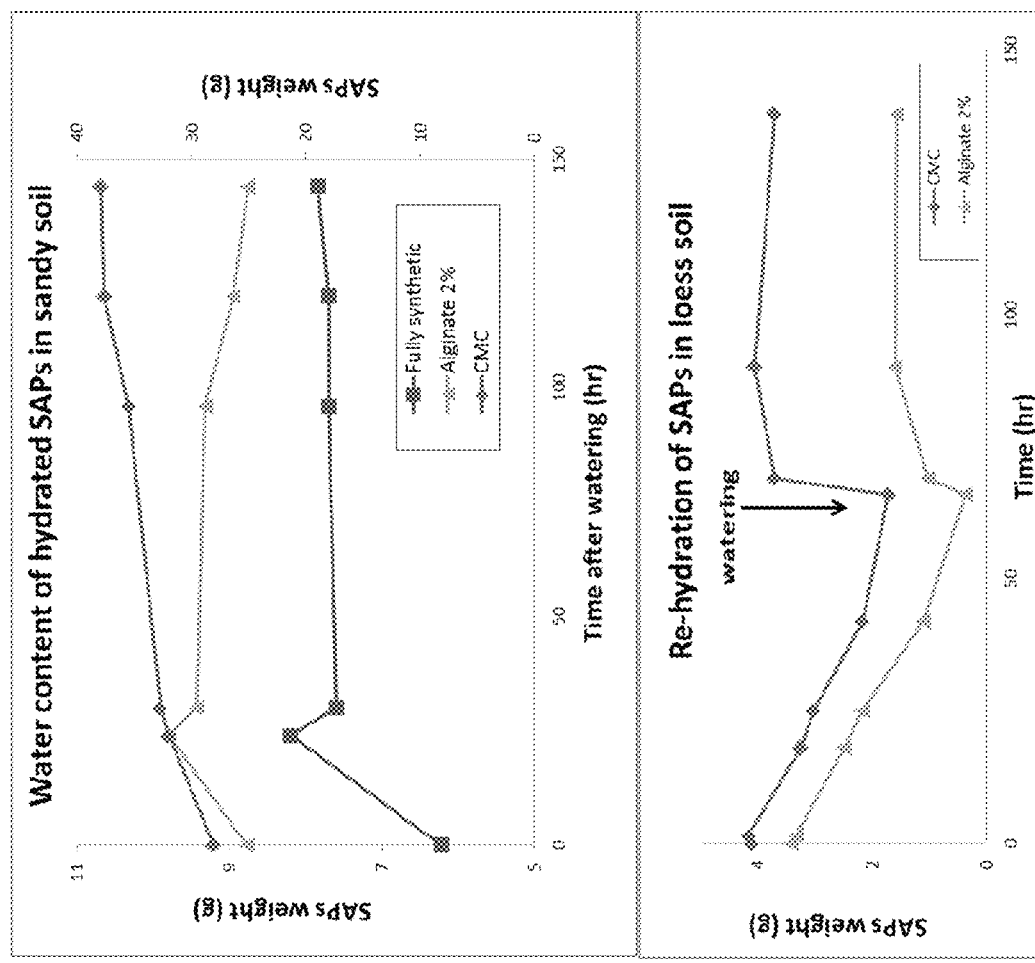

The present invention provides a bead comprising:
i) an external zone comprising a super absorbent polymer (SAP) that is capable of absorbing at least about 5 times its weight in water, surrounding
ii) at least one internal zone comprising a core that contains at least one agrochemical,
wherein the external zone is permeable to oxygen when hydrated, or the internal zone is formulated to release the at least one agrochemical into the external zone over a period of at least about one week when the hydrogel of the external zone is hydrated.

In some embodiments, the SAP is capable of absorbing at least about 50, 75, 80, 85, 90, 95, 100, 200, 300, 400, 500, or 1000 times its weight in water.

In some embodiments, the SAP is permeable to oxygen.

In some embodiments, the SAP is permeable to oxygen such that it maintains at least about 6 mg/L of dissolved oxygen in the SAP when it is hydrated.

In some embodiments, the SAP when fully hydrated is at least about 70, 75, 80, 85, 90, 95, or 100% as permeable to oxygen as hydrated alginate or hydrated semi-synthetic CMC.

In some embodiments, the SAP is an aerogel, a hydrogel or an organogel.

In some embodiments, the SAP is a hydrogel.

In some embodiments, the external zone further comprises a polymer, a porous inorganic material, a porous organic material, or any combination thereof.

In some embodiments, the internal zone further comprises an aerogel, a hydrogel, an organogel, a polymer, a porous inorganic material, a porous organic material, or any combination thereof.

In some embodiments, roots of a crop plant are capable of penetrating the hydrogel when the hydrogel is about 5%, 10%, 15%, 20%, 25%, 30%, 35%, 40%, 45%, 50%, or 5-50% hydrated.

In some embodiments, roots of a crop plant are capable of penetrating the hydrogel when the hydrogel is about 5%, 10%, 15%, 20%, 25%, 30%, 35%, 40%, 45%, 50%, or 5-50% hydrated.

In some embodiments, roots of a crop plant are capable of growing within the hydrogel when the hydrogel is hydrated.

In some embodiments, roots of a crop plant are capable of growing within the hydrogel when the hydrogel is about 5%, 10%, 15%, 20%, 25%, 30%, 35%, 40%, 45%, 50%, or 5-50% hydrated.

In some embodiments, roots of a crop plant are capable of growing within the hydrogel when the hydrogel is hydrated.

In some embodiments, roots of a crop plant are capable of growing within the hydrogel when the hydrogel is about 5%, 10%, 15%, 20%, 25%, 30%, 35%, 40%, 45%, 50%, or 5-50% hydrated.

In some embodiments, the crop plant is wheat plant.

In some embodiments, the crop plant is maize plant.

In some embodiments, the crop plant is a soybean plant.

In some embodiments, the crop plant is a rice plant.

In some embodiments, the crop plant is a barley plant.

In some embodiments, the crop plant is a cotton plant.

In some embodiments, the crop plant is a pea plant.

In some embodiments, the crop plant is a potato plant.

In some embodiments, the crop plant is a tree crop plant.

In some embodiments, the crop plant is a vegetable plant.

In some embodiments, hydrogel is capable of repeated swelling cycles that each comprises hydration followed by dehydration.

In some embodiments, the hydrogel is capable of repeated swelling cycles in soil that each comprise hydration followed by dehydration while in the soil.

In some embodiments, is in the shape of a sphere or an equivalent polyhedron.

In some embodiments, the bead is in the shape of a sphere or an equivalent polyhedron after repeated swelling cycles.

In some embodiments, the hydrogel, when hydrated, maintains at least about 75%, 80%, 85%, 90%, or 95% of its water content over a period of at least about 25, 50, 100, or 150 hours in soil.

In some embodiments, the hydrogel, when hydrated, maintains at least about 75%, 80%, 85%, 90%, or 95% of its water content over a period of at least about 25, 50, 100, or 150 hours in sandy soil.

In some embodiments, the hydrogel, when hydrated, maintains at least about 75%, 80%, 85%, 90%, or 95% of its volume over a period of at least about 25, 50, 100, or 150 hours in soil.

In some embodiments, the hydrogel, when hydrated, maintains at least about 75%, 80%, 85%, 90%, or 95% of its volume over a period of at least about 25, 50, 100, or 150 hours in sandy soil.

In some embodiments, the hydrogel, when hydrated, maintains its shape over a period of at least about 25, 50, 100, or 150 hours in soil.

In some embodiments, the hydrogel, when hydrated, maintains spherical shape over a period of at least about 25, 50, 100, or 150 hours in sandy soil.

In some embodiments, the hydrogel, when hydrated, maintains its shape after repeated swelling cycles that each comprises hydration followed by dehydration.

In some embodiments, the hydrogel, when hydrated maintains its shape after at least 3 swelling cycles that each comprises hydration followed by dehydration.

In some embodiments, the SAP is biodegradable.

In some embodiments, when hydrated in soil, the external zone of the bead has a pH or osmotic pressure that differs from the pH or osmotic pressure of the surrounding soil by at least about 10%.

In some embodiments, the external zone does not contain the at least one agrochemical before the bead is hydrated for the first time.

In some embodiments, the external zone also contains the at least one agrochemical.

In some embodiments, the amount of the at least one agrochemical in the external zone is about 5%, 10%, 15% or 20% (w/w) of the amount of the at least one agrochemical that is in the internal zone.

In some embodiments, the bead has a maximum diameter of about 1, 2, 3, 4, 5, 6, 7, 8, 9, or 10 cm when the SAP of the external zone is about 5%, 10%, 15%, 20%, 25%, 30%, 35%, 40%, 45%, 50%, or 5-50% hydrated.

In some embodiments, when the SAP of the external zone is about 5%, 10%, 15%, 20%, 25%, 30%, 35%, 40%, 45%, 50%, or 5-50% hydrated, the weight of the external zone is at least about 2, 3, 4, 5, 6, 7, 8, 9, or 10 times greater than the weight of the internal zone.

In some embodiments, the hydrogel is a synthetic hydrogel, a natural carbohydrate hydrogel, or a pectin or protein hydrogel, or any combination thereof.

In some embodiments, the synthetic hydrogel comprises acrylamide, an acrylic derivative, or any combination thereof.

In some embodiments, the natural carbohydrate hydrogel comprises agar, cellulose, chitosan, starch, hyaluronic acid, a dextrine, a natural gum, a sulfated polysaccharide, or any combination thereof.

In some embodiments, the pectin or protein hydrogel comprises gelatin, a gelatin derivative, collagen, a collagen derivative, or any combination thereof.

In some embodiments, the hydrogel comprises a natural super absorbent polymer (SAP), a poly-sugar SAP, a semi-synthetic SAP, a fully-synthetic SAP, or any combination thereof.

In some embodiments, the hydrogel comprises a combination of at least one natural SAP and at least one semi-synthetic or synthetic SAP.

In some embodiments, the hydrogel comprises a poly-sugar SAP.

In some embodiments, the poly-sugar SAP is alginate.

In some embodiments, the alginate is at least about 0.2% alginate.

In some embodiments, the hydrogel comprises a semi-synthetic SAP.

In some embodiments, the semi-synthetic SAP is a CMC-g-polyacrylic acid SAP.

In some embodiments, the Carboxymethyl cellulose (CMC) grafted polyacrylic acid SAP comprises 6% CMC relative to the acrylic monomers (Acrylamide-acrylic), 6% CMC relative to acrylic acid, 25% CMC relative to acrylic acid, or CMC 50% AA.

In some embodiments, the SAP is other than alginate or a k-carrageenan cross-linked-polyacrylic acid SAP.

In some embodiments, the SAP is a k-carrageenan cross-link polyacrylic acid SAP.

In some embodiments, the hydrogel comprises a fully synthetic SAP.

In some embodiments, the fully synthetic SAP is acrylic acid or acrylic amide or any of the combinations thereof.

In some embodiments, the external zone further comprises at least one oxygen carrier that increases the amount of oxygen in the external zone compared to a corresponding external zone not comprising the oxygen carrier.

In some embodiments, the at least one oxygen carrier is a perfluorocarbon.

In some embodiments, the internal zone comprises an organic polymer, a natural polymer, or an inorganic polymer, or any combination thereof.

In some embodiments, the at least one core is coated with at least one coat compound.

In some embodiments, the at least one coat compound dissolves into the SAP when the SAP is hydrated.

In some embodiments, the at least one coat compound slows the rate at which the at least one agrochemical dissolves into the SAP when the SAP is hydrated.

In some embodiments, the at least one coat compound is silicate or silicon dioxide.

In some embodiments, the at least one coat compound is the at least one agrochemical.

In some embodiments, the at least one core comprises a polymer.

In some embodiments, the polymer is a highly cross-linked polymer.

In some embodiments, the highly cross-linked polymer is a poly-sugar or a poly-acrylic polymer.

In some embodiments, the at least one core comprises a filler.

In some embodiments, the filler comprises a cellulosic material, a cellite, a polymeric material, a silicon dioxide, a phyllosilicate, a clay mineral, metal oxide particles, porous particles, or any combination thereof.

In some embodiments, the filler comprises a phyllosilicate of the serpentine group.

In some embodiments, the a phyllosilicate of the serpentine group is antigorite $(Mg_3Si_2O_5(OH)_4)$, chrysotile $(Mg_3Si_2O_5(OH)_4)$, or lizardite $(Mg_3Si_2O_5(OH)_4)$.

In some embodiments, the filler comprises a clay mineral, which is halloysite $(Al_2Si_2O_5(OH)_4)$, kaolinite $(Al_2Si_2O_5(OH)_4)$, illite $((K,H_3O)(Al,mg,Fe)_2(Si,Al)_4O_{10}[(OH)_2,(H_2O)])$, montmorillonite $((Na,Ca)_{0.33}(Al,Mg)_2Si_4O_{10}(OH)_2.nH_2O)$, vermiculite $((MgFe,Al)_3(Al,Si)_4O_{10}(OH).4H_2O)$, talc $(Mg_3Si_4O_{10}(OH)_2)$ palygorskite $((Mg,Al)_2Si_4O_{10}(OH).4(H_2O)$, or pyrophyllite $(Al_2Si_4O_{10}(OH)_2)$.

In some embodiments, the filler comprises a phyllosilicate of the mica group.

In some embodiments, the a phyllosilicate of the mica group is biotite $(K(mg,Fe)_3(AlSi_3)O_{10}(OH)_2)$, muscovite $(KAl_2(AlSi_3)O_{10}(OH)_2)$, phlogopite $(KMg_3(AlSi_3)O_{10}(OH)_2)$, lepidolite $(K(Li,Al)_{2-3}(AlSi_3)O_{10}(OH)_2)$, margarite $(CaAl_2(Al_2Si_2)O_{10}(OH)_2)$, glauconite $((K,Na)(Al,Mg,Fe)_2(Si,Al)_4O_{10}(OH)_2)$, or any combination thereof.

In some embodiments, the filler comprises a phyllosilicate of the chlorite group.

In some embodiments, the a phyllosilicate of the chlorite group is chlorite $((Mg,Fe)_3(Si,Al)_4O_{10}(OH)_2.(Mg,Fe)(OH)_6)$.

In some embodiments, the filler forms a beehive-like structure.

In some embodiments, the beehive-like structure is microscopic.

In some embodiments, the filler comprises clay.

In some embodiments, the filler comprises zeolite.

In some embodiments, the core comprises at least about 0.05, 0.1, 0.2, 0.3, 0.4, 0.5, 0.6, 0.7, 0.8, 0.9, or 1 grams of the at least one agrochemical.

In some embodiments, the core is about 30%, 35%, 40%, 45%, 50%, 55%, or 60% of the at least one agrochemical by weight.

In some embodiments, the at least one core is biodegradable.

In some embodiments, the internal zone contains one core.

In some embodiments, the at least one agrochemical is:
i) at least one fertilizer compound;
ii) at least one pesticide compound,
iii) at least one hormone compound;
iv) at least one drug compound;
v) at least one chemical growth agents; and/or
vi) at least one microelement.

In some embodiments, the at least one fertilizer compound is a natural fertilizer.

In some embodiments, the at least one fertilizer compound is a synthetic fertilizer.

In some embodiments, the at least one pesticide compound is:
i) at least one insecticide compound;
ii) at least one nematicide compound;
iii) at least one herbicide compound; and/or
iv) at least one fungicide compound.

In some embodiments, the at least one insecticide compound is imidacloprid.

In some embodiments, the at least one herbicide compound is pendimethalin.

In some embodiments, the at least one fungicide compound is azoxystrobin.

In some embodiments, the at least one nematicide compound is fluensulfone.

In some embodiments, the at least one fertilizer compound is $PO_4$, $NO_3$, $(NH_4)_2SO_2$, $NH_4H_2PO_4$, and/or KCl.

In some embodiments, the at least one fertilizer compound comprises multiple fertilizer compounds which include $PO_4$, $NO_3$, $(NH_4)_2SO_2$, $NH_4H_2PO_4$, and/or KCl.

In some embodiments, the at least one agrochemical is at least one fertilizer compound and at least one pesticide compound.

In some embodiments, the at least one agrochemical is at least one pesticide compound.

In some embodiments, the at least one agrochemical is at least one fertilizer compound.

In some embodiments, the at least one pesticide compound is at least one pesticide compound that is not suitable for application to an agricultural field.

In some embodiments, the at least one pesticide compound that is not suitable for application to an agricultural field is too toxic to be applied to an agricultural field.

In some embodiments, the at least one pesticide compound is toxic to animals other than arthropods or mollusks when applied to an agricultural field in an amount that is sufficient to kill an arthropod or a mollusk.

In some embodiments, the at least one agrochemical is released from the core of the internal zone over a period of at least about one week when the SAP of the external zone is hydrated.

In some embodiments, the at least one agrochemical is released from the core of the internal zone over a period of at least about one week when the SAP of the external zone is hydrated.

In some embodiments, the at least one agrochemical is released from the internal zone into the external zone over a period of at least about 2, 3, 4, 5, 6, 7, 8, 9, 10, or 20 weeks when the SAP of the external zone is hydrated.

In some embodiments, the at least one agrochemical is released from the internal zone into the external zone over a period of at least about 2, 3, 4, 5, 6, 7, 8, 9, 10, or 20 weeks when the SAP of the external zone is about 5%, 10%, 15%, 20%, 25%, 30%, 35%, 40%, 45%, 50%, or 5-50% hydrated.

In some embodiments, when the SAP of the bead is hydrated and the bead is in soil, the at least one agrochemical diffuses from the surface of the bead into the surrounding soil at a linear rate beginning about 25 days after hydration.

In some embodiments, when the SAP of the bead is hydrated and the bead is in soil, the at least one agrochemical diffuses from the surface of the bead into the surrounding soil for at least about 50 or 75 days after hydration.

In some embodiments, the bead is not hydrated.

In some embodiments, the bead contains less than about 35%, 30%, 25%, 20%, 15%, or 10% water by weight.

In some embodiments, the bead further comprises an interface zone between the internal zone and the external zone, which interface zone is formed by at least one insoluble salt or solid, at least one cross-linking agent, or at least one inorganic compound.

In some embodiments, diffusion between the external zone and the internal zone is limited by altering the pH or the cation concentration in the internal zone, the external zone, or the interface zone.

In some embodiments, diffusion between the external zone and the internal zone is limited by altering the pH and/or cation concentration in the internal zone or the external zone.

In some embodiments, the pH in the internal zone or the external zone is altered by a buffer.

In some embodiments, the pH in the internal zone, the external zone, or the interface zone is altered by a buffer.

The present invention provides a method of growing a plant, comprising adding at least one bead of the invention to the medium in which the plant is grown.

In some embodiments, the medium in which the plant is grown comprises soil.

In some embodiments, the medium in which the plant is grown is soil.

In some embodiments, the soil comprises sand, silt, clay, or any combination thereof.

In some embodiments, the soil is clay, loam, clay-loam, or silt-loam.

The present invention provides a method of growing a plant, comprising adding multiple beads of the invention to the medium of the plant, wherein the multiple beads comprise three fertilizer compounds, such that the total N, P, and K content as $(NH_4)_2SO_2$, $NH_4H_2PO_4$, and $KCl$ in the medium as part of the beads is about 25, 5, and 30 $g/m^2$, respectively.

The present invention provides a method of generating an artificial zone with predetermined chemical properties within the root zone of a plant, comprising:
  i) adding at least two different beads to the root zone of the plant; or
  ii) adding at least two different beads to the anticipated root zone of the medium in which the plant is anticipated to grow,
wherein at least one of the at least two different beads is a bead of an embodiment of the invention.

In some embodiments, each of the at least two different beads contains at least one agrochemical that is not contained within one of the other at least two different beads.

In some embodiments, the plant is grown in a field.

In some embodiments, the plant is a crop plant.

In some embodiments, the crop plant is a grain or a tree crop plant.

In some embodiments, the crop plant is a fruit or a vegetable plant.

In some embodiments, the plant is a banana, barley, bean, cassava, corn, cotton, grape, orange, pea, potato, rice, soybean, sugar beet, tomato, or wheat plant.

The present invention provides a microenvironment (μ-Environment) for plant growth comprising two parts, wherein part A is located inside part B, whereas;
  Part A is a controlled release reservoir of additive with a weight of at least 0.05 gr, and wherein;
  Part B is a microenvironment comprised of at least 90% water when fully swelled, and its weight is at least 5 times larger than part A.

In some embodiments, the microenvironment is synthesized so that one of the moisture, pH or osmotic pressure inside the microenvironment is different by at least 10% from the surrounding soil; and plant roots can penetrate and grow inside the microenvironment volume.

In some embodiments, parts A and B are fabricated from materials consisting of polymers, aerogels, hydrogels, organogels, porous inorganic, porous organic material or a combination thereof.

In some embodiments, part A is selected from the group consisting of organic polymer, natural polymer, inorganic polymer or a combination thereof.

In some embodiments, part A also comprises components in the solids form.

In some embodiments, part A contains fillers selected from the group consisting from clays, metal oxide particles, porous particles or a combination thereof.

In some embodiments, additive is selected from the group consisting of nutrients, agrochemicals, pesticides, microelements, drugs or a combination thereof.

In some embodiments, part A comprises both structural materials and functional materials.

In some embodiments, part B contains no fraction of said additive, or at least 10 times lower concentration of said additives then in Part A, when added to the soil.

In some embodiments, part B is selected from the group consisting of organic polymer, natural polymer, inorganic polymer or a combination thereof.

In some embodiments, part B contains fillers selected from the group consisting from air, porous particles or a combination thereof.

In some embodiments, the microenvironment is transported to the field in a dry form, containing less than 30% water.

In some embodiments, the dimension of the microenvironment is at least 30 mL in the fully swelled form.

In some embodiments, the additive concentration in Part A is at least 50%.

In some embodiments, after contacting Part A and Part B, an interface is formed between the two parts by means of: the formation of insoluble salts or solids, cross linking agents, inorganic component chemistry or by altering pH or cation concentration so as to limit the diffusion between the two parts and the combination thereof.

In some embodiments, part A also comprises components in the solids form.

In some embodiments, part A comprises both structural materials and functional materials.

In some embodiments, the distance between the μ-Environment and the plant seed is between 0.1 to 500 centimeters.

In some embodiments, the distance between the µ-Environment and the plant seed is between 0.1 to 500 centimeters. In some embodiments, the distance between the µ-Environment and the plant seed is about 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100 centimeters.

Non-limiting examples of structural materials of the present invention are materials that give the structure of the system for example water, aerogels, treated starch, treated cellulose, polymers, superadsorbents and the functional materials are the materials consumed by the plant for example, a fertilizer compound.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means±10% of the numerical value or range recited or claimed, unless the context requires a more limited range.

Plants provided by or contemplated for use in embodiments of the present invention include both monocotyledons and dicotyledons. In some embodiments, a plant is a crop plant. As used herein, a "crop plant" is a plant which is grown commercially. In some embodiments, the plants of the present invention are crop plants (for example, cereals and pulses, maize, wheat, potatoes, tapioca, rice, sorghum, millet, cassava, barley, or pea), or other legumes. In some embodiments, the crop plants may be grown for production of edible roots, tubers, leaves, stems, flowers or fruit. The plants may be vegetable or ornamental plants. Non-limiting examples of crop plants of the invention include: *Acrocomia aculeata* (macauba palm), *Arabidopsis thaliana*, *Aracinis hypogaea* (peanut), *Astrocaryum murumuru* (murumuru), *Astrocaryum vulgare* (tucumã), *Attalea geraensis* (Indaiárateiro), *Attalea humilis* (American oil palm), *Attalea oleifera* (andaiá), *Attalea phalerata* (uricuri), *Attalea speciosa* (babassu) *Avena sativa* (oats), *Beta vulgaris* (sugar beet), *Brassica* sp. such as *Brassica carinata*, *Brassica juncea*, *Brassica napobrassica*, *Brassica napus* (canola), *Camelina sativa* (false flax), *Cannabis sativa* (hemp), *Carthamus tinctorius* (safflower), *Caryocar brasiliense* (pequi), *Cocos nucifera* (Coconut), *Crambe abyssinica* (Abyssinian kale), *Cucumis melo* (melon), *Elaeis guineensis* (African palm), *Glycine max* (soybean), *Gossypium hirsutum* (cotton), *Helianthus* sp. such as *Helianthus annuus* (sunflower), *Hordeum vulgare* (barley), *Jatropha curcas* (physic nut), *Joannesia princeps* (arara nut-tree), *Lemna* sp. (duckweed) such as *Lemna aequinoctialis*, *Lemna disperma*, *Lemna ecuadoriensis*, *Lemna gibba* (swollen duckweed), *Lemna japonica*, *Lemna minor*, *Lemna minuta*, *Lemna obscura*, *Lemna paucicostata*, *Lemna perpusilla*, *Lemna tenera*, *Lemna trisulca*, *Lemna turionifera*, *Lemna valdiviana*, *Lemna yungensis*, *Licania rigida* (oiticica), *Linum usitatissimum* (flax), *Lupinus angustifolius* (lupin), *Mauritia flexuosa* (buriti palm), *Maximiliana maripa* (inaja palm), *Miscanthus* sp. such as *Miscanthus×giganteus* and *Miscanthus sinensis*, *Nicotiana* sp. (tabacco) such as *Nicotiana tabacum* or *Nicotiana benthamiana*, *Oenocarpus bacaba* (bacaba-doazeite), *Oenocarpus bataua* (pataua), *Oenocarpus distichus* (bacaba-de-leque), *Oryza* sp. (rice) such as *Oryza sativa* and *Oryza glaberrima*, *Panicum virgatum* (switchgrass), *Paraqueiba paraensis* (mari), *Persea amencana* (avocado), *Pongamia pinnata* (Indian beech), *Populus trichocarpa*, *Ricinus communis* (castor), *Saccharum* sp. (sugarcane), *Sesamum indieum* (sesame), *Solanum tuberosum* (potato), *Sorghum* sp, such as *Sorghum bicolor*, *Sorghum vulgare*, *Theobroma grandiforum* (cupuassu), *Trifolium* sp., *Trithrinax brasiliensis* (Brazilian needle palm), *Triticum* sp. (wheat) such as *Triticum aestivum*, *Zea mays* (corn), alfalfa (*Medicago sativa*), rye (*Secale cerale*), sweet potato (*Lopmoea batatus*), cassava (*Manihot esculenta*), coffee (*Cofea* spp.), pineapple (*Anana comosus*), citris tree (*Citrus* spp.), cocoa (*Theobroma cacao*), tea (*Camellia senensis*), banana (*Musa* spp.), avocado (*Parses americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*) and almond (*Prunus amygdalus*).

Unless stated otherwise or required otherwise by context, "hydrated" means at least about 5% hydrated.

As used herein, a "microenvironment" or "µ-Environment" means a media located within the root zone of an agricultural field or a garden plant loaded with at least one agrochemical, encourages root growth and uptake activity within its internal periphery. Non-limiting examples of agrochemicals include pesticides, including insecticides, herbicides, and fungicides. Agrochemicals may also include natural and synthetic fertilizers, hormones and other chemical growth agents.

In some embodiments, the medium may comprise multiple sub-zones, such as:
i) an Internal Zone; and
ii) an External Zone.

In some embodiments, the internal zone is formulated to release the at least one agrochemical into the external zone over a period of at least about one week when the hydrogel of the external zone is hydrated. In some embodiments, the internal zone is formulated to release the at least one agrochemical into the external zone over a period of at least about 2, 3, 4, 5, 6, 7, 8, 9, 10, 11, 12, 13, 14, 15, 16, 17, 18, 19, or 20 weeks when the hydrogel of the external zone is hydrated. The internal zone may be formulated to control the release of the at least one agrochemical into the external zone by a variety of means described herein. For example, the at least one agrochemical may be incorporated into a dense polymer in the core of the internal zone, from which the at least one agrochemical diffuses when external zone is hydrated. Additionally, the core may be coated with a compound or compounds that slow the rate of the at least one agrochemical's diffusion into the external zone. In some embodiments, the coat compound may diffuse into the external zone when the external zone is hydrated, thereby slowing the rate of the at least one agrochemical's diffusion into and/or through the external zone. In some embodiments, the core comprises a filler comprising the at least one agrochemical, from which the at least one agrochemical diffuses. In some embodiments, the at least one agrochemical diffuses from the core or the filler at a linear rate. The filler may slow the rate of the at least one agrochemical from the core. In some embodiments filler may has a physical structure, such as a beehive-like structure, into which the at least one agrochemical is incorporated, and from which the at least one agrochemical slowly diffuses. Bentonite is a non-limiting example of a filler having a beehive-like structure that is useful in embodiments of the present invention.

The internal zone may contain the input (fertilizer or other agrochemical) in a structure that controls its release into the external zone. The release rate is designed to meet plant demands throughout the growing season. In some embodiments, no input residuals remain at the end of a predetermined action period.

In some embodiments, the internal zone comprises one or more fertilizers and/or other agrochemicals such as nitrogen, phosphorus, potassium, fungicide, insecticide, etc., in a beehive like structure made from highly cross linked polymer coated with silica or highly cross linked poly acrylic acid/poly sugar with a clay filler. In some embodiments, the internal zone comprises fertilizer and/or at least one other agrochemical in a beehive like structure with or without an external coating.

In some embodiments, the external zone is a super absorbent polymer (SAP) surrounding the internal zone, which attracts the growth and uptake activity of plant roots. In some embodiments, the external zone is a super absorbent polymer—made from CMC-g-poly(acrylic acid)/celite composite system or modified corn starch cross linked poly (acrylic acid). An external zone may be referred to herein as a "shell."

External zones of the present invention are sustainable in soils, and encourage root penetration, uptake activity, and growth and/or development in the external zone. In some embodiments, a super absorbent polymer may serve as the external zone since during watering it can absorb soil moisture, swell and maintain its high water content over long period of time. These features establish a zone where gradual transition of chemical concentration exists between the internal zone to the periphery allowing root uptake activity during the bead or microenvironment's life cycle. In some embodiments, the external zone has features such as mechanical resistance (in order to maintain it's shape and geometry in the soil); swelling cycle capability (capable of repeated hydration and dehydration in response to soil water content); oxygen permeability—(maintaining sufficient oxygen level to support root activity, such as root development); and root penetration (allowing the growth of roots into it).

Materials that may be used in the present invention include but are not limited to: 1) clay 2) zeolite 3) tuff 4) fly ash 5) hydrogel 6) foam.

In some embodiments, a microenvironment of the present invention serves as a buffer for soil type and pH to provide universal root growth environment. In some embodiments, a microenvironment of the present invention contains needed materials and nutrients in the desired conditions, such as but not limited to water, fertilizers, drugs, and other additives.

Oxygen Permeability

Aspects of the present invention relate to external zones having SAPs that are permeable to oxygen when hydrated. Roots use oxygen for growth and development (Drew, 1997; Hopkins 1950). Therefore, the oxygen permeability of a SAP is an important factor in determining whether it will support root growth and development within a bead external zone that comprises the SAP.

Without wishing to be bound by any scientific theory, since hydrogels of the present invention supply water, nutrients and weak resistance, the data hereinbelow show that provided the gas diffusion is high enough, roots will develop in most types of small-volume hydrogels, installed in a field soil. For example, alginate hydrogel, which is suitably permeable to oxygen, encourages root development, whereas starch hydrogel, which is poorly permeable to oxygen does not encourage root development. Additionally, semi-synthetic CMC is also suitably permeable to oxygen. The ability of oxygen to diffuse into external zones of the present invention is important for root development within them.

Aspects of the present invention relate to the selection of SAPs, such as hydrogels, that are sufficiently permeable to oxygen when hydrated. Oxygen permeability may be measured to determine whether a hydrated SAP is sufficiently permeable to oxygen for use in embodiments of the present invention. In some embodiments, the SAP is permeable to oxygen such that it supports root growth and/or development. In some embodiments, the SAP when hydrated is at least about 70, 75, 80, 85, 90, 95, or 100% as permeable to oxygen as hydrated alginate. In some embodiments, the SAP when hydrated is at least about 70, 75, 80, 85, 90, 95, or 100% as permeable to oxygen as hydrated semi-synthetic CMC.

Oxygen permeability may be measured according to assays that are well known in the art. Non-limiting examples of methods that may be useful for measuring oxygen permeability of SAPs of the invention are described in Aiba et al. (1968) "Rapid Determination of Oxygen Permeability of Polymer Membranes" Ind. Eng. Chem. Fundamen., 7(3), pp 497-502; Yasuda and Stone (1962) "Permeability of Polymer Membranes to Dissolved Oxygen" Cedars-Sinai Medical Center Los Angeles Calif. Polymer Div, 9 pages, available from www.dtic.mil/cgi-bin/GetTRDoc?Location=U2&doc.GetTRDoc.pdf&AD=AD0623983; Erol Ayranci and Sibel Tunc (March 2003) "A method for the measurement of the oxygen permeability and the development of edible films to reduce the rate of oxidative reactions in fresh foods" Food Chemistry Volume 80, Issue 3, Pages 423-431; and Compañ et al. (July 2002) "Oxygen permeability of hydrogel contact lenses with organosilicon moieties" Biomaterials Volume 23, Issue 13, Pages 2767-2772, the entire contents of each of which are incorporated herein by reference. The permeability of a SAP may be measured when it is partially or hydrated, e.g. when the SAP is 5%, 10%, 15%, 20%, 25%, 30%, 35%, 40%, 45%, 50%, or 5-50% hydrated.

Mechanical Resistance

In preferred embodiments of the present invention, the external zone of a bead is both i) sufficiently permeable to oxygen to encourage root growth, and ii) does not disintegrate in soil. In especially preferred embodiments, the external zone of a bead is mechanically resistant, i.e., is capable of repeated swelling cycles in soil without fragmenting in the soil. In particularly preferred embodiments, all of the SAP of the external zone remains part of the external zone after repeated swelling cycles.

Despite alginate's permeability to oxygen, external zones consisting of alginate are not suitable in preferred embodiments of the invention because alginate tends to disintegrate in soil. However, semi-synthetic CMC, which does not tend to disintegrate and is capable of repeated swelling cycles without fragmenting in soil (i.e., is mechanically resistant), is suitable for use in external zones in preferred embodiments the invention.

Implementation of Microenvironments

Some embodiments of the present invention comprise the following phases:

Phase 1: Banding and incorporating into the upper soil profile.

Phase 2: Following watering (rainfall and/or irrigation) the super absorbent polymer absorbs moisture from the soil and swells; water penetrates the coating and dissolve the fertilizer and/or other agrochemical(s) which then diffuse toward the periphery.

Phase 3: Roots grow, develop, and remain in the external zone where uptake lasts a predetermined period.

Methods for Testing Properties of Bead Shells

The following is a non-limiting example of a method that may be used to test the properties of bead shells (i.e. external zones).

- Distribute shells of different sizes in a pot. In some embodiments, shells of three sizes are used. The shells may have a dry radius of, e.g., 0.5, 1, 1.5, 2. 2.5, 3, 3.5, 4, 4.5, or 5 cm). In some embodiments a 10, 11, 12, 13, 14, 15, 20, 25, or 30 liter pot is used. In some embodiments the shells are distributed in the pot with soil. In some embodiments, the soil is sandy soil.
- Monitor the final size and geometry of the shells following watering. In some embodiments, the final geometry is spherical.
- Installing ceramic suction cups to mimic roots water uptake and applying suction through the syringes.
- Altering watering frequency over time (e.g., from high—few times per day to low—once a week).
- Monitoring the volume of water in the syringes and water drained from the bottom of the pot over time.

The following is another non-limiting example of a method that may be used to test the properties of bead shells (i.e. external zones).

- Distribute shells of one size (base, e.g. on findings from the method described above phase) in a transparent cell. In some embodiments, the cell is made of Perspex—and is 60×2×30 cm). In some embodiments, the shells are distributed with soil. In some embodiments, the soil is sandy soil.
- Monitoring root location and shell status. In some embodiments, root location and shell status is monitored by photography or/and scanning.
- Repeat with shells with/without nutrients.
- Monitoring roots location to conclude if roots attract by nutrients or water.
- Altering watering frequency over time (e.g., from high—few times per day to low—once a week).

Methods for Testing Properties of Beads

The following is a non-limiting example of a method that may be used to test the properties of bead shells (i.e. external zones).

- Growing a plant in a pot. In some embodiments, the pot is a 10, 11, 12, 13, 14, 15, 20, 25, or 30 liter pot.
- Installing filter paper cups to monitor concentrations in the root zone and drainage over time.

Additionally:

- Growing a plant in a transparent cell with mixture of beads soil. In some embodiments, the soil is sandy soil.
- Add dying agents to beads which are sensitive to environmental conditions (e.g., pH, Salinity, or N, P, and K).
- Altering watering frequency over time (e.g. from high—few times per day to low—once a week).

Super Absorbent Polymers

Super Absorbent Polymers are polymers that can absorb and retain extremely large amounts of a liquid relative to their own mass. Non-limiting examples of SAPs that are useful in embodiments of the subject invention are described in K. Horie, M. Báron, R. B. Fox, J. He, M. Hess, J. Kahovec, T. Kitayama, P. Kubisa, E. Maréchal, W. Mormann, R. F. T. Stepto, D. Tabak, J. Vohlídal, E. S. Wilks, and W. J. Work (2004). "Definitions of terms relating to reactions of polymers and to functional polymeric materials (IUPAC Recommendations 2003)". Pure and Applied Chemistry 76 (4): 889-906; Kabiri, K. (2003). "Synthesis of fast-swelling superabsorbent hydrogels: effect of crosslinker type and concentration on porosity and absorption rate". European Polymer Journal 39 (7): 1341-1348; "History of Super Absorbent Polymer Chemistry". M2 Polymer Technologies, Inc. (available from www.m2polymer.com/html/history_of_superabsorbents.html); "Basics of Super Absorbent Polymer & Acrylic Acid Chemistry". M2 Polymer Technologies, Inc. (available from www.m2polymer.com/html/chemistry_sap.html); Katime Trabanca, Daniel; Katime Trabanca, Oscar; Katime Amashta, Issa Antonio (September 2004). Los materiales inteligentes de este milenio: Los hidrogeles macromoleculares. Síntesis, propiedades y aplicaciones. (1 ed.). Bilbao: Servicio Editorial de la Universidad del País Vasco (UPV/EHU); and Buchholz, Fredric L; Graham, Andrew T, ed. (1997). Modern Superabsorbent Polymer Technology (1 ed.). John Wiley & Sons, the entire contents of each of which are hereby incorporated herein by reference.

Non-limiting examples of hydrogels that are useful in embodiments of the subject invention are described in Mathur et al., 1996. "Methods for Synthesis of Hydrogel Networks: A Review" Journal of Macromolecular Science, Part C: Polymer Reviews Volume 360 Issue 2, 405-430; and Kabiri et al., 2010. "Superabsorbent hydrogel composites and nanocomposites: A review" Volume 32, Issue 2, pages 277-289, the entire contents of each of which are hereby incorporated herein by reference.

Agrochemicals

Fertilizers

A fertilizer is any organic or inorganic material of natural or synthetic origin (other than liming materials) that is added to a plant medium to supply one or more nutrients that promotes growth of plants.

Non-limiting examples of fertilizers that are useful in embodiments of the subject invention are described in Stewart, W. M.; Dibb, D. W.; Johnston, A. E.; Smyth, T. J. (2005). "The Contribution of Commercial Fertilizer Nutrients to Food Production". Agronomy Journal 97: 1-6.; Erisman, Jan Willem; M A Sutton, J Galloway, Z Klimont, W Winiwarter (October 2008). "How a century of ammonia synthesis changed the world". Nature Geoscience 1 (10): 636.; G. J. Leigh (2004). The world's greatest fix: a history of nitrogen and agriculture. Oxford University Press US. pp. 134-139; Glass, Anthony (September 2003). "Nitrogen Use Efficiency of Crop Plants: Physiological Constraints upon Nitrogen Absorption". Critical Reviews in Plant Sciences 22 (5): 453; Vance; Uhde-Stone & Allan (2003). "Phosphorus acquisition and use: critical adaptations by plants for securing a non renewable resource", New Mythologist (Blackwell Publishing) 157 (3): 423-447. Moore, Geoff (2001). Soilguide—A handbook for understanding and managing agricultural soils. Perth, Western Australia: Agriculture Australia. pp. 161-207; Häussinger, Peter; Reiner Lohmüller, Allan M. Watson (2000). Ullmann's Encyclopedia of Industrial Chemistry, Volume 18. Weinheim, Germany: Wiley-VCH Verlag GmbH & Co. KGaA. pp. 249-307.; Carroll and Salt, Steven B. and Steven D. (2004). Ecology for Gardeners. Cambridge: Timber Press.; Enwall, Karin; Laurent Philippot,2 and Sara Hallini (December 2005). "Activity and Composition of the Denitrifying Bacterial Community Respond Differently to Long-Term Fertilization". Applied and Environmental Microbiology (American Society for Microbiology) 71(2): 8335-8343.; Birkhofera, Klaus; T. Martijn Bezemerb, c, d, Jaap Bloeme, Michael Bonkowskia, Søren Christensenf, David Duboisg, Fleming Ekelundf, Andreas Flielβbachh, Lucie Gunstg, Katarina Hedlundi, Paul Mäderh, Juha Mikolaj, Christophe Robink, Heikki Setäläj, Fabienne Tatin-Frouxk, Wim H. Van der Puttenb, c and Stefan Scheua (September 2008). "Long-term organic farming fosters below and aboveground biota: Implications for soil quality, biological control and productivity". Soil Biology and Biochemistry (Soil Biology and Biochemistry) 40 (9): 2297-2308.; Lal, R. (2004). "Soil Carbon Sequestration Impacts on Global Climate Change and Food Security". Science (Science (journal)) 304 (5677): 1623-7.; and Zublena, J. P.; J. V. Baird, J. P. Lilly (June 1991). "Soil-Facts—Nutrient Content of Fertilizer and Organic Materials". North Carolina Cooperative Extension Service. (available from www.soil.ncsu.edu/publications/Soilfacts/AG-439-18/), the entire contents of each of which are hereby incorporated herein by reference.

Non-limiting examples of fertilizers which may be useful in embodiments of the present invention include Ammonium nitrate, Ammonium sulfate, anhydrous ammonia, calcium nitrate/urea, oxamide, potassium nitrate, urea, urea sulfate, ammoniated superphosphate, diammonium phosphate, nitric phosphate, potassium carbonate, potassium metaphosphate, calcium chloride, magnesium ammonium phosphate, magnesium sulfate, ammonium sulfate, potassium sulfate, and others disclosed herein.

Pesticides

Pesticides are substances or mixtures of substances capable of preventing, destroying, repelling or mitigating any pest. Pesticides include insecticides, nematicides, herbicides and fungicides.

Insecticides

Insecticides are pesticides that are useful against insects, and include but are not limited to organochloride, organophosphate, carbamate, pyrethroid, neonicotinoid, and ryanoid, insecticides.

Non-limiting examples of insecticides that are useful in embodiments of the subject invention are described in van Emden H F, Pealall D B (1996) Beyond Silent Spring, Chapman & Hall, London, 322 pp; Rosemary A. Cole "Isothiocyanates, nitriles and thiocyanates as products of autolysis of glucosinolates in Cruciferae" Phytochemutry, 1976. Vol. 15, pp. 759-762; and Robert L. Metcalf "Insect Control" in Ullmann's Encyclopedia of Industrial Chemistry" Wiley-VCH, Weinheim, 2002, the entire contents of each of which are incorporated herein by reference.

Nematicides

Nematicides are pesticides that are useful against plant-parasitic nematodes.

Non-limiting examples of nematicides that are useful in embodiments of the subject invention are described in D. J. Chitwood, "Nematicides," in Encyclopedia of Agrochemicals (3), pp. 1104-1115, John Wiley & Sons, New York, N.Y., 2003; and S. R. Gowen, "Chemical control of nematodes: efficiency and side-effects," in Plant Nematode Problems and their Control in the Near East Region (FAO Plant Production and Protection Paper—144), 1992, the entire contents of each of which are incorporated herein by reference.

Herbicides

Herbicides are pesticides that are useful against unwanted plants. Non-limiting examples of herbicides that are useful in embodiments of the subject invention include 2,4-D, aminopyralid, atrazine, clopyralid, dicamba, glufosinate ammonium, fluazifop, fluroxypyr, imazapyr, imazamox, metolachlor, pendimethalin, picloram, and triclopyr.

Fungicides

Fungicides are pesticides that are useful against fungi and/or fungal spores.

Non-limiting examples of fungicides that are useful in embodiments of the subject invention are described in Pesticide Chemistry and Bioscience edited by G. T Brooks and T. R Roberts. 1999. Published by the Royal Society of Chemistry; Metcalfe, R. J. et al. (2000) The effect of dose and mobility on the strength of selection for DMI (sterol demethylation inhibitors) fungicide resistance in inoculated field experiments. Plant Pathology 49: 546-557; and Sierotzki, Helge (2000) Mode of resistance to respiration inhibitors at the cytochrome bcl enzyme complex of *Mycosphaerella fijiensis* field isolates Pest Management Science 56:833-841, the entire contents of each of which are incorporated herein by reference.

Microelements

Non-limiting examples of microelements that are useful in embodiments of the subject invention include iron, manganese, boron, zinc, copper, molybdenum, chlorine, sodium, cobalt, silicon, and selenium nickel.

Hormones

Plant hormones may be used to affect plant processes.

Non-limiting examples of plant hormones that are useful in embodiments of the subject invention include but are not limited to, auxins (such as heterouaxin and its analogues, indolylbutyric acid and α-naphthylacetic acid), gibberellins, and cytokinins.

All publications and other references mentioned herein are incorporated by reference in their entirety, as if each individual publication or reference were specifically and individually indicated to be incorporated by reference, Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1

The External Zone

Four specific criteria were defined as the following, where each condition was tested experimentally:

Mechanical resistance—maintain shape and geometry in the soil

Swelling cycles—hydrate and dehydrate in corresponds to soil water content

Oxygen permeability—maintain sufficient oxygen level to root activity

Root penetration—allows the growth of root into it.

Mechanical resistance was tested by flushing water throughout a container filled with SAP and sand soil. Initial, final weights and dimensions were recorded. A pass mark was accepted for SAP that maintains a single element and didn't washed away or split into several parts. Three groups of SAP were synthesized and tested:

| Group | Poly sugar | Semi synthetic | Fully synthetic |
|---|---|---|---|
| | | SAPs | |
| Type | Alginate | CMC-g-poly (acrylic acid)/Celite composite system Carboxymethyl cellulose grafted polyacrylics acid with Celite as a filler. k-Carrageenan poly(acrylic acid)SAP | Acrylic Acid/Acryl Amide |

Each type of SAP was formulated with variable mixture of poly sugars, crosslinked agents, filler and additive. Moreover, samples were oven dried and immersed in distilled water in order to calculate the equilibrium swelling (ES) according to the following equation:

$$ES = \frac{\text{weight of swollen gel} - \text{weight of Dried gel}}{\text{weight of Dried gel}}$$

TABLE 1 summarizes the findings of the mechanical resistance tests:

| SAP- Group | SAP- type | Bis-AAm/AA | % PS/AA | NaOH | ES |
|---|---|---|---|---|---|
| Semi-synthetic | CMC | 0.75-1.25 | 50-75 | 15-25 | 73-467 |
| synthetic | k-Carrageenan | 1.6-2.5 | 33-66 | — | 25-72 |
| Poly sugar | Alginate - 2% | — | 100 | — | 38 |
| Fully synthetic | Acrylic (AA/AM) | — | 0 | — | 180 |

"Big-AAm/AA" means (Acrylic acid crosslinkad with Bis acrylamide," "% PS/AA, semi-synthetic Polysugar -acrylic acid hydrogel" and "ES" means "equilibrium swelling." "Alginate - 2%." means 2% in water when hydrated.

1) Poly Sugar:

16 gr of sodium alginate was dissolved in 800 ml distilled water at 50° C. using mechanical stirrer (1000 RPM). Then 20 gr from the alginate solution was added in to 50 ml beaker, then 10 gr of 0.1 M solution of CaCl$_2$, was added in to the beaker (CaCl$_2$ served as the cross-linking agent). The beads were left in the solution for a 12 hr.

2) CMC-g-Poly (Acrylic Acid)/Celite

Various amounts of CMC (Carboxymethyl cellulose sodium Salt) (0.5-2 g) were dissolved in 25 ml distilled water and were added to a 100 ml beaker with magnetic stirrer. The beaker was immersed in a temperature controlled water bath preset at 80° C. After complete dissolution of CMC, various amounts of Celite powder (0.3-0.6 g in 5 ml water) were added (if any) to the solution and allowed to stir for 10 min. Then, certain amounts of AA (Acrylic Acid) (2-3 ml) and MBA (N—N methylene bis acrylamide) (0.025-0.1 g in 5 ml water) were added to the reaction mixture and allowed to stir for 5 min. Then the initiator solution (0.07 g APS (Ammonium persulfate) in 5 ml water) was added to the mixture, the mixture was placed immersed in a temperature controlled water bath preset at 85° C. for 40 minutes to complete polymerization. To neutralize (0-100%) acrylic groups, appropriate amount of NaOH (0-1 gr in 5 ml water) was added. The obtained gel was poured to excess nonsolvent ethanol (80 ml) and remained for 1 h.

3) k-Carrageenan (kC) Cross-Linked-Poly(Acrylic Acid)

0.5-1 gr of kC (k-Carrageenan) was dissolved in 25 mL of distilled water, which was under vigorous stirring in a 100 ml beaker with a magnetic stirrer. The flask was immersed in a temperature controlled water bath at 80° C. After complete dissolution of kC to form a homogeneous solution, certain amounts of AA (Acrylic Acid), and MBA (N—N methylene bis acrylamide) simultaneously added to the reaction mixture. Afterward, the solution was stirred and purged with nitrogen for 2 min to remove the dissolved oxygen. Then, a definite amount of APS (Ammonium persulfate) solution was added dropwise to the reaction flask under continuous stirring to generate free radicals. The reaction maintained at this temperature for 1 h to complete polymerization.

4) Fully Synthetic System (a Sample for Akm):

AAm (Acrylamide) (10 g) was mix with 25 ml distilled water at room temperature in a 50 ml beaker equipped with magnetic stirrer. Then MBA (N—N Methylene his acrylamide) (0.008 gr) was added into the mixture and allowed to stir for 10 min. Then an initiator solution was added (0.07 g SPS (Sodium persulfate)). The mixture was placed into 5 ml template (4 gr solution each) and placed in a convention furnace (85° C.) for 20 min. The product was washed overnight with ethanol (80 ml) to obtain the polymerized shell.

Starch Systems—Sample for Non-Growing Media

1) Modified Starch Cross-Linked Poly(Acrylic Acid)

1-2.5 gr of Corn starch dissolved in deionized 20 ml water in 100 ml beaker at room temperature. The combination was mixed until a uniform mixture was formed. 2-3 gr AA (Acrylic acid) was added to the cooled mixture and the resulting mixture was stirred for five minutes. Next, 1-3 gr AAm (acrylamide) was added to the mixture, and the resulting mixture was stirred for five minutes. Then 0.005-0.01 gr of MBA (N—N methylene his acrylamide) dissolved in 5 ml of deionized water was added to the mixture, and the resulting mixture was stirred for five minutes. Lastly, 0.005 gr of APS (ammonium persulfate) dissolved in 0.5 ml of deionized water; was added to the mixture and the resulting mixture was stirred while being heated to 80° C. The mixture was held at that temperature and stirred for approximately 15 minutes. Because the resulting viscous mass was acidic, the mixture was neutralized by titration with 45% potassium hydroxide (KOH) at room temperature. Titration continued until a pH of 7.0 was reached, which required addition of between about 0.2-16 g 45% KOH.

2) Similar Process to the CMC-AA System.

(Exchanging CMC with corn-starch):

1 gr of corn Starch was dissolved in 25 ml distilled water and were added to a 100 ml beaker with magnetic stirrer. The beaker was immersed in a temperature controlled water bath preset at 80° C. Then 2 ml of AA (Acrylic Acid) and MBA (N—N methylene bis acrylamide) (0.015 g in 5 ml water) were added to the reaction mixture and allowed to stir for 5 min. Then the initiator solution (0.07 g APS (Ammonium persulfate) in 5 ml water) was added to the mixture, the mixture was placed immersed in a temperature controlled water bath preset at 85° C. for 40 minutes to complete polymerization. NaOH (0.5 gr in 5 ml water) was added in order to neutralize acrylic groups. The obtained gel was poured to excess nonsolvent ethanol (80 ml) and remained for 1 h.

Swelling cycles of selected formulations in water and two types of soil were tested. The ability of the SAPs to absorb water in relatively short time is an important physical property that allows maintaining its functionality in the soil throughout its life cycle. The following graphs present the swelling behavior of the different SAPS upon hydration-dehydration cycles in water. The ES of the investigated SAPs stay constant during three cycles, meaning good mechanical properties.

The water content of several SAPs in sandy silica soil was measured following watering over a time period that is a typical watering cycle of crops and plants. The various SAPS gain water from the soil in the first 24 hours following by a mild decrease/increase over the next 125 hours. When SAPs were introduced to air dry loess soil, initially it went under rapid de hydration, yet watering the soil reverse the process and water were absorbed from the soil the soil recovery percentage were 99 and 50. The results indicate that all groups of SAPs can maintain their moisture in the sandy soil over a watering cycle and that CMC base SAPs can fully recovery from extreme dry condition in soil.

Figure 3:
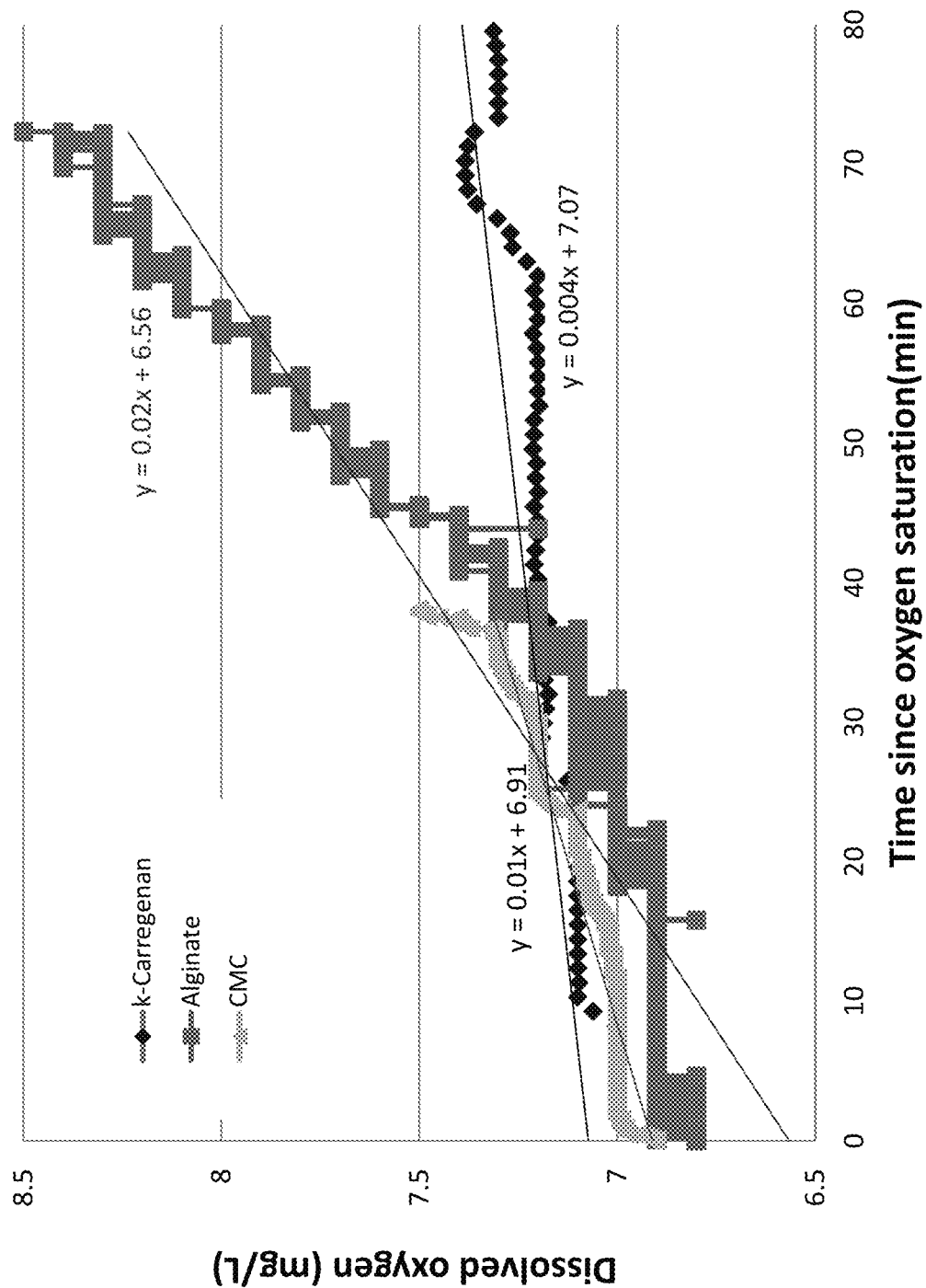
FIG. 3. Dissolved oxygen level in the water reservoir opposite the oxygen saturated water.

Oxygen permeability of the SAPS was studied by measuring dissolved oxygen in water that was exposed to oxygen saturated water across a SAP. Altering dissolved oxygen level was done by bubbling nitrogen or oxygen gases into the water reservoir located opposite the sensor. SAPs made from Alginate and CMC showed an order magnitude more oxygen permeability than SAP of k-carrageenan (FIG. 3).

Dissolved Oxygen Test:

Oxygen electrode place into a pre-swelled hydrogel in a 100 ml beaker. The dissolved oxygen inside the hydrogel was measured during $N_2$ bubbling or $O_2$ bubbling (~0.5 liter per minute) as a function of time.

Figure 13:
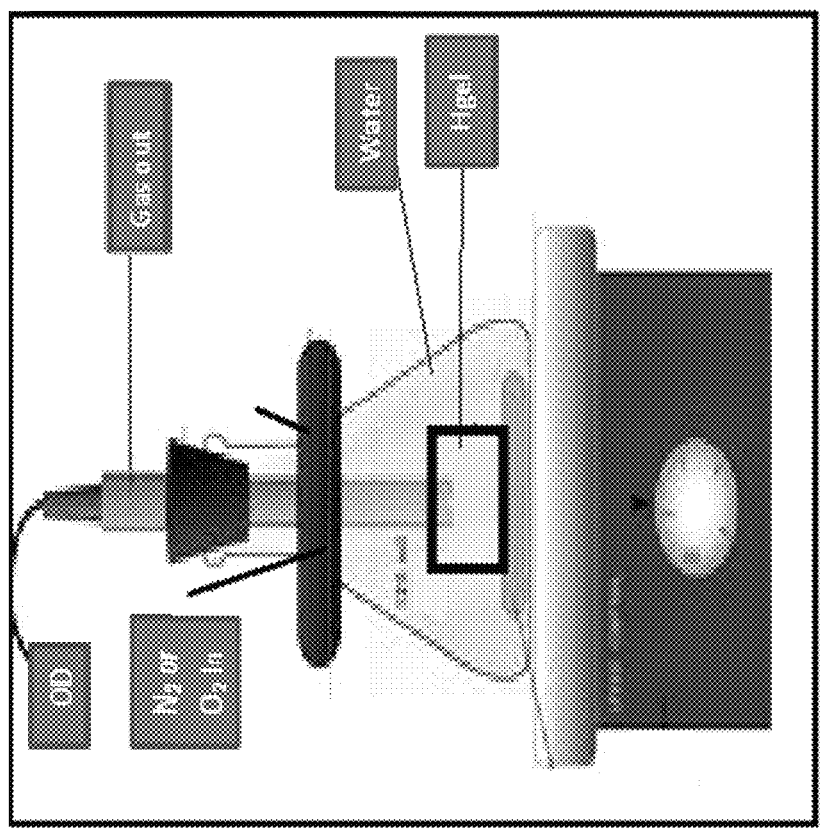
FIG. 13. Dissolved Oxygen System.

The $O_2$ measurements made by Lutron WA2017SD Analyzer with dissolved oxygen probe 0-20 mg/L, 0-50° C. The Dissolved Oxygen System is shown in FIG. 13.

Figure 9:
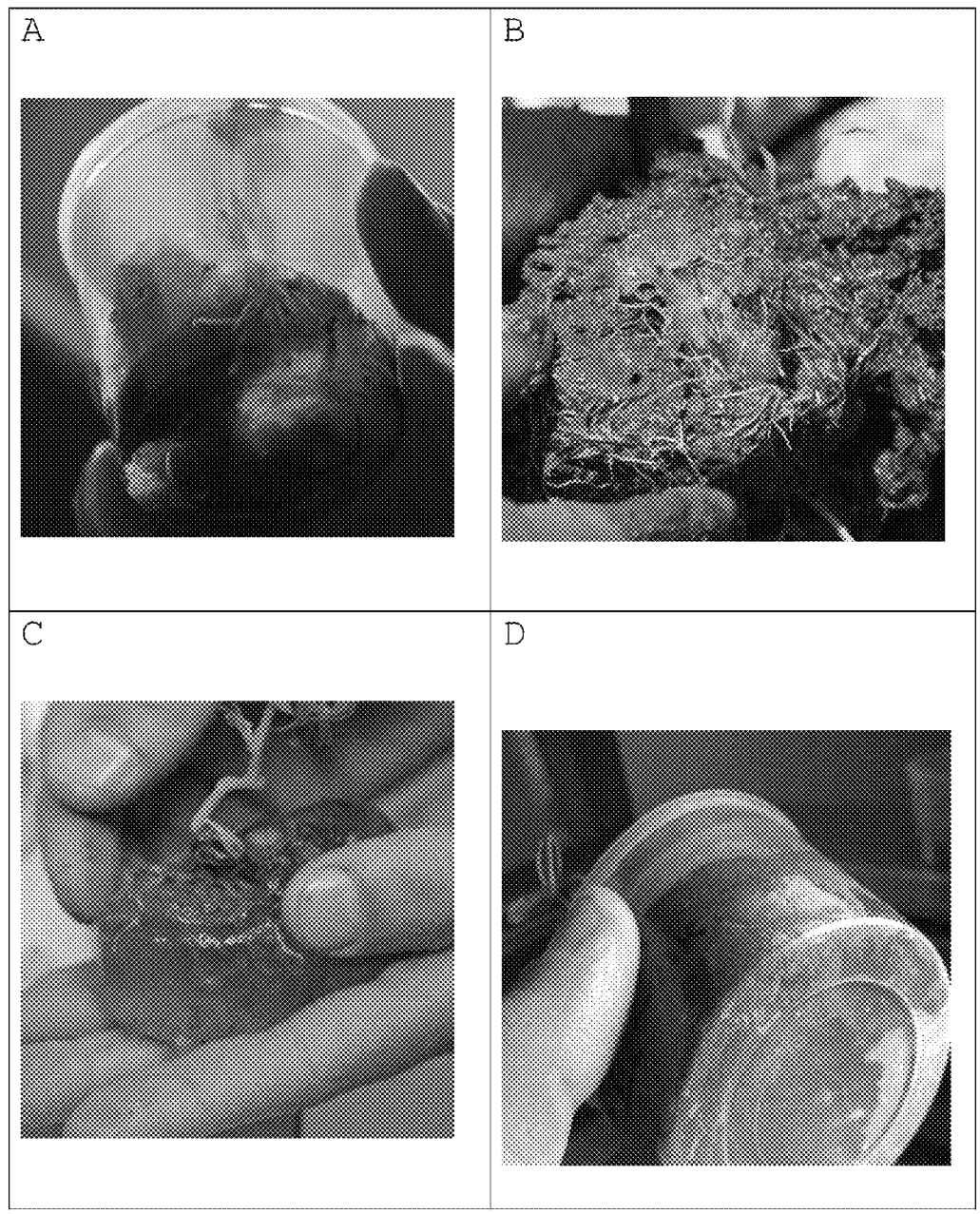
FIG. 9. (A) Pea roots growth in CMC—Lab. (B) Corn roots growth in Alginate—Lab. (C) Pea root growth in k-Carrageenan—Lab. (D) Pea root growth on CMC—Lab. (E) Corn root grown in Fully synthetic—Lab. (F) Corn root grown in Fully synthetic—Lab. (G) Corn roots growth in Alginate—Lab.
Figure 9:
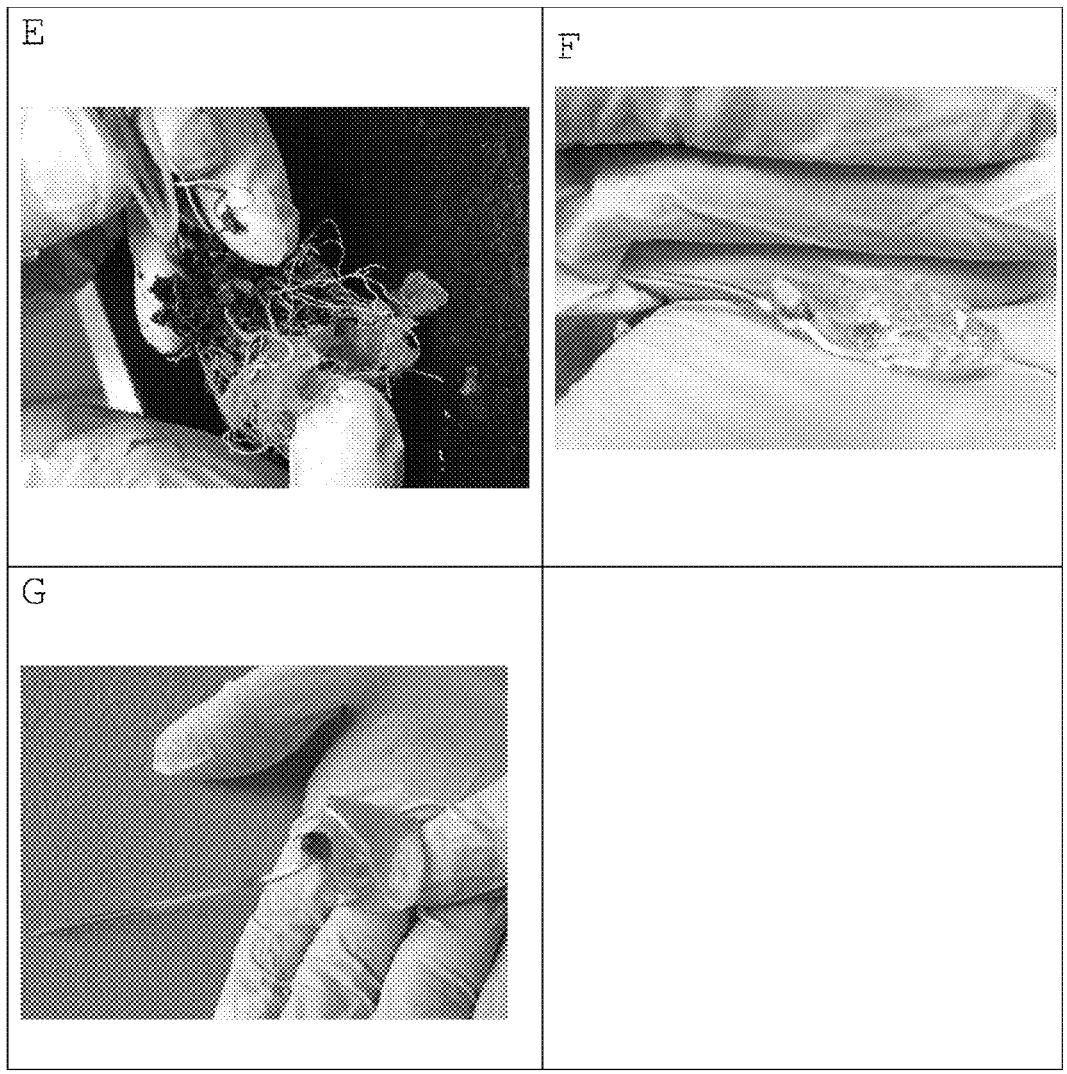
Figure 10:
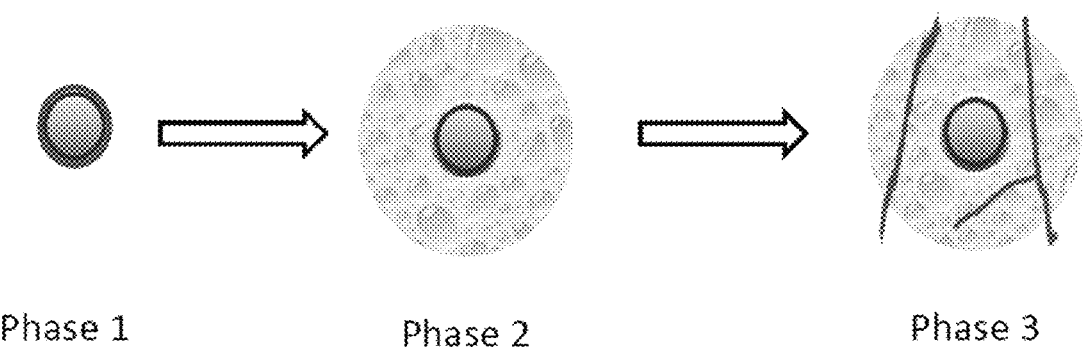
FIG. 10. Phase 1: Banding and incorporating dry "beads", made from an external zone (hydrogel-blue) and internal zone (coated minerals-greenish/red) into the upper soil profile. Phase 2: Following watering, the beads swell (up to, e.g., 5 cm in diameter) and agrochemicals diffuse to the external zone & soil. Phase 3: Roots grow and are sustained in/near the external zone, and uptake lasts a few weeks (6-8).
Figure 11:
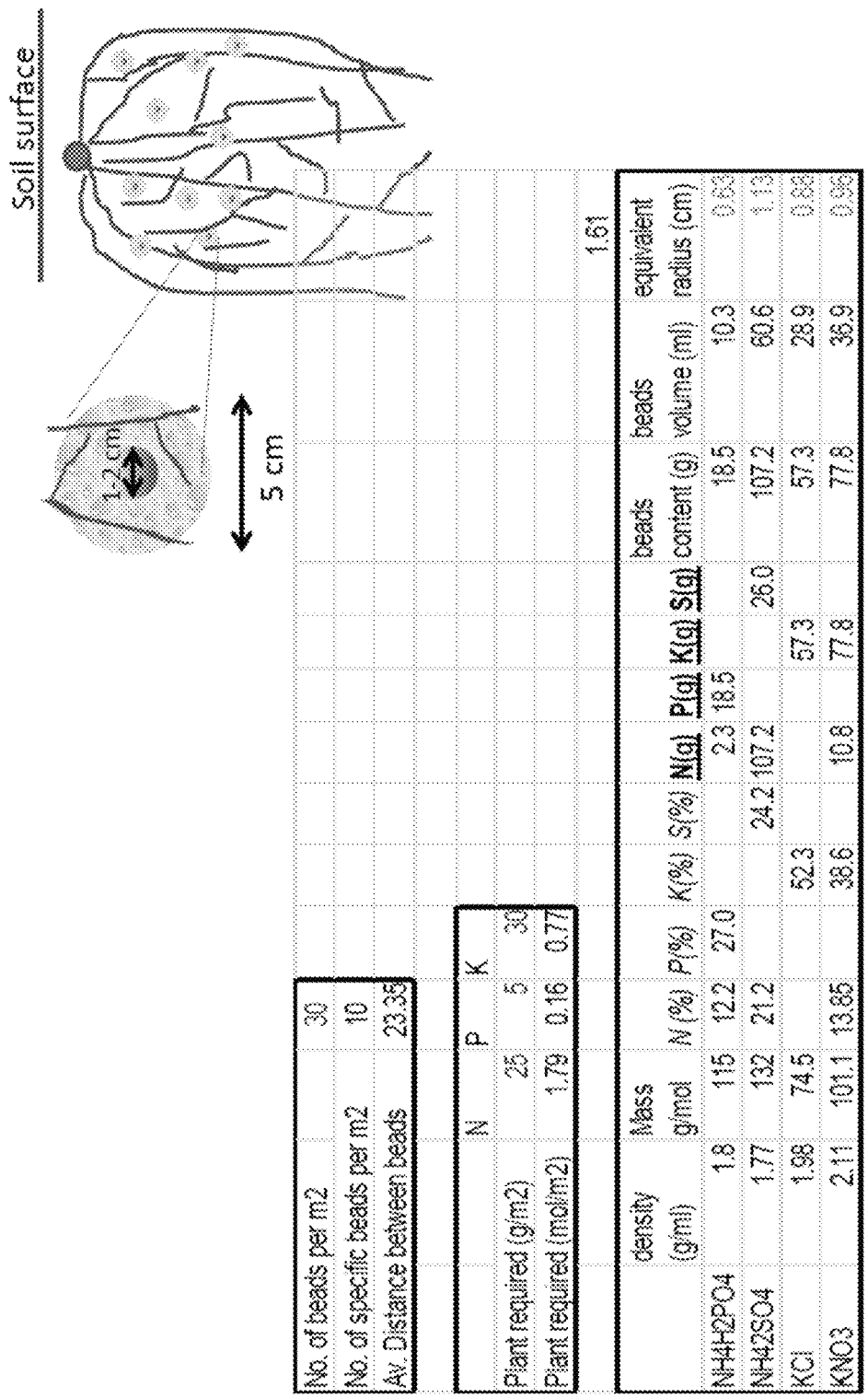
FIG. 11. Non-limiting examples of bead content and dimensions.

Root penetration was evaluated visually from a series of experiments, where various crops grew in pots filled with organic soil surrounded a micro environment. Table 2 summarizes the observations presented in FIG. 9:

| SAPs | Crop | Roots on the surface of micro-environment | Roots penetrated into the micro-environment | Roots developed in the micro-environment |
|---|---|---|---|---|
| Poly Sugar - Alginate | Pea | − | + | + |
| Semi synthetic-CMC | Corn, Pea, | + | + | − |
| Semi synthetic-k-Carrageenan | Pea | + | + | − |
| Fully synthetic | Corn | + | + | − |

Example 2

The Internal Zone

Three mechanisms were developed and evaluated to address the criteria of i) release rate of agrochemicals from the internal zone over a growing season, and ii) that no input residuals remain at the end of a predetermined action period. All the three, are based on integrating the input into a very dense polymer as the basic mechanism to slow down diffusion, in conjunction to a secondary mechanism that will additionally decrease the diffusion rate:

1) Highly Cross Linked Polymer with silicon coating (xLP-Si);
2) Highly Cross linked Poly Acrylic/poly sugar with filler (xLP-F); and
3) Hybrid system (SiCLP-).

Figure 4:
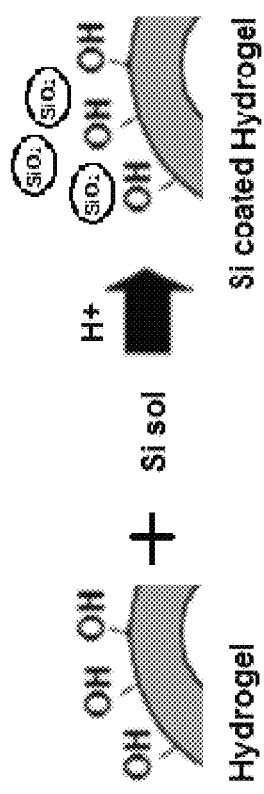
FIG. 4. Silica coating process on poly sugar beads.

The first mechanism is based on precipitation of silica, originated from silica water, on the surface of the polymer (FIG. 4).

Figure 5:
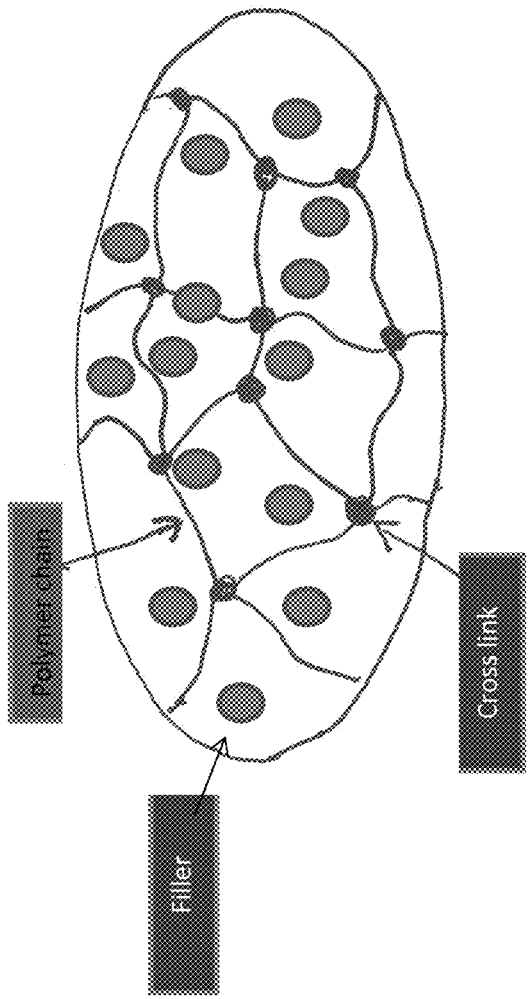
FIG. 5. Beehive like structure made by the Bentonite filler.

The second mechanism is based on filler, made from bentonite, integrated into the polymer and decreases sharply its diffusion properties (FIG. 5).

Figure 6:
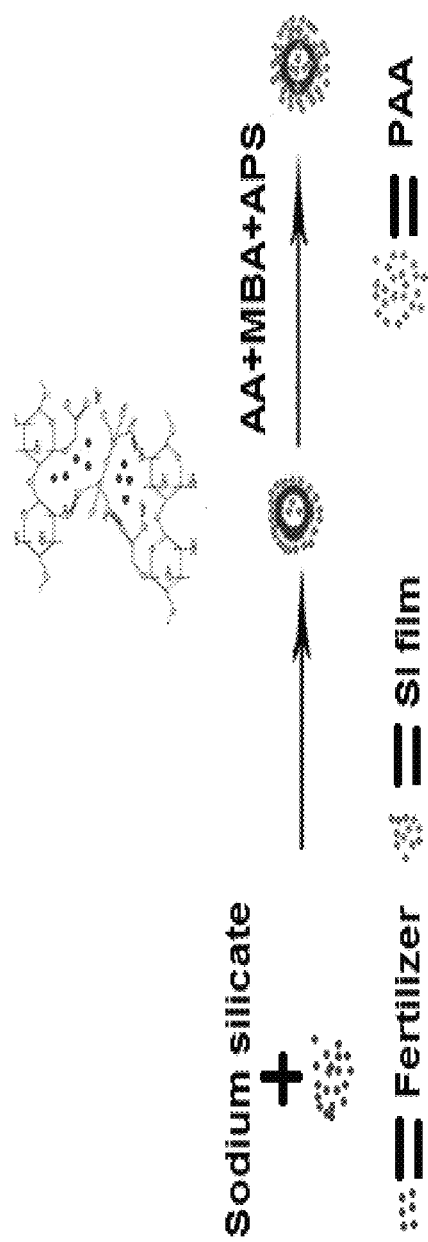
FIG. 6. Schematic illustration of the hybrid encapsulation method.

The third mechanism is to mix the silica with the acrylic while synthesizing the polymer in order to alter its diffusion coefficient (FIG. 6).

The reduction in diffusion properties by each mechanism was experimentally tested. The internal zone was located in a free water reservoir where the concentration of a certain input (Nitrogen or Phosphorus) was measured over time.

Figure 7:
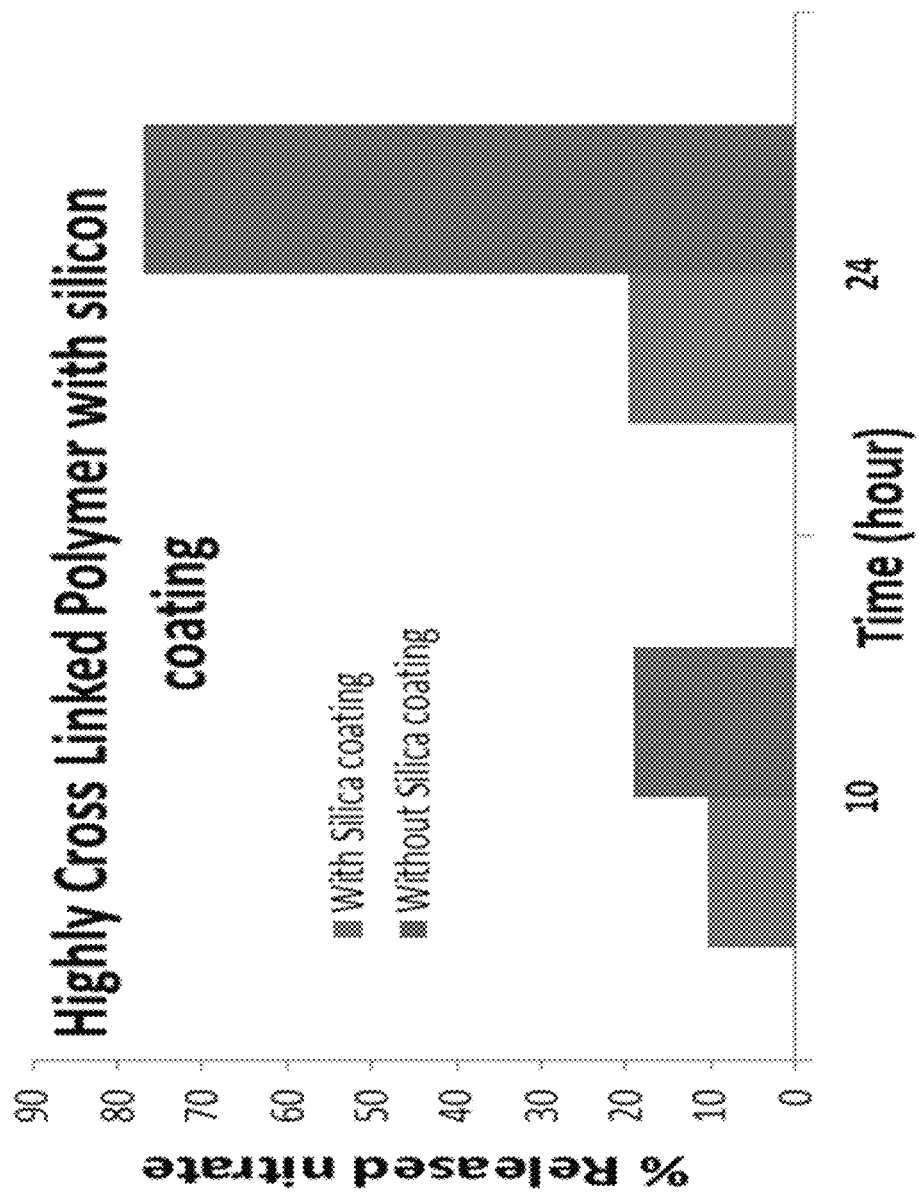
FIG. 7. Release of nitrate from internal zone without (red) and with (blue) Silica coating.
Figure 8:
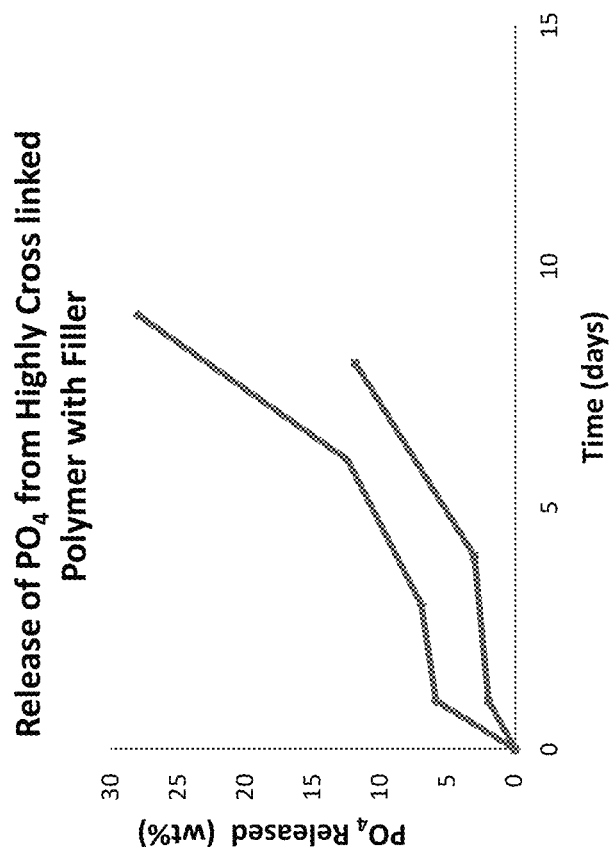
FIG. 8. Release of $PO_4$ from internal zone incorporated with Bentonite filler over time.

The release of nitrate from cornstarch internal zone with (blue) and without (red) silica coating is presented in FIG. 7. A reduction of diffused nitrate was measured in the first 24 hours.

Alternatively, the mixed silica mechanism yielded release of nitrate and phosphorus in the scale of weeks, as well.

Discussion

High rates of inefficient agrochemical use are attributed to unknown root distribution, spatial variability in soil structure and texture (i.e. mineral and organic matter content), temporal variability of soil conditions (i.e. temperature, moisture, pH, aeration and salinity), temporal changes in plant demands of fertilizers and agrochemicals (i.e. species, development stage, root morphology), and climatic fluctuations throughout the growing season (i.e. rainfall, temperature, humidity, radiation and wind).

Soil-less medium, where optimal conditions for efficient uptake by roots are maintained, is implemented solely in small scale containers in greenhouses. This practice is not feasible as a solution for large scale fields.

An overall goal of the present invention is supplying fertilizers and other agrochemicals (e.g. nitrogen, phosphorus, potassium, fungicides, insecticides, etc.) directly to plant roots at required amounts and timing regardless of soil and crop types and conditions.

Availability and uptake of fertilizer from commercial products are dramatically affected by soil due to the pH and reactions with various cations. The present invention relates to universal additives and formulations that are not affected by soil type or pH, due to the formation of microenvironment.

A problem with the additions of small SAP beads (super-absorbent polymer with diameter of 1 cm) is a fast diffusion of the additives into the soil. In contrast to the SAP beads that are currently used, beads of the present invention have a bigger size (in some embodiments, diameter of 12 cm), which prevents this problem. Aspects of the present invention also prevent properties from changing due to salts entering the soil. Furthermore, the concepts herein based on the formation of microenvironment in the field, contrast other technology that use hydrogels as a solid replacement.

Aspects of the present invention that are advantageous and unique over current technologies and practices include but are not limited to:

Universally—embodiments of the present invention are not dependant on temporal and spatial variations of soil, crop and weather.

Simplicity—embodiments of the present invention relate to a single application using conventional equipment.

Economy—embodiments of the present invention save labor and the amount of agrochemical input (fertilizers and otheragrochemicals, and energy) for the farmer.

Sustainability—embodiments of the present invention protect the environment (water bodies and atmosphere) from contamination as a result of leaching, runoff and volatilization of agrochemicals.

The present invention provides microenvironments that encourage or promote root growth or development in different soil types. Root growth and development are a function of moisture, oxygen nutrients and mechanical resistance. The data herein showed alginate preformed markedly well with respect to root development. However, additional formulations (semi-synthetic CMC and fully synthetic-acrylic acid and acrylamide) show root growth as well. Aspects of the present invention relate to microenvironments that provide, moisture and nutrients, while being mechanically resistant and permeable to oxygen.

REFERENCE

Drew M. C., 1997. Oxygen deficiency and root metabolism: Injury and acclimation under hypoxia and anoxia. ANNUAL REVIEW OF PLANT PHYSIOLOGY AND PLANT MOLECULAR BIOLOGY Volume: 48 Pages: 223-250.

Habarurema and Steiner, 1997. Soil suitability classification by farmers in southern Rwanda. Geoderma Volume 75, Issues 1-2, Pages 75

Hopkins H. T., 1950. Growth and nutrient accumulation as controlled by oxygen supply to plant roots. Plant Physiology, 25(2): 193-209.

Nicholson S. E. and Farrar T. J., 1994. The influence of soil type on the relationships between NDVI, rainfall, and soil moisture in semiarid Botswana. I. NDVI response to rainfall. Remote Sensing of Environment Volume 50, Issue 2, Pages 107-120

Shaviv A., Mikkelsen R. L. 1993. Controlled-release fertilizers to increase efficiency of nutrient use and minimize environmental degradation—A review. Fert. Res. 35, 1-12.

What is claimed is:

1. A bead comprising:
   i) an external zone comprising a super absorbent polymer (SAP) that is capable of absorbing at least about 5 times its weight in water, surrounding
   ii) at least one internal zone comprising a core that contains at least one agrochemical,
   wherein the external zone is permeable to oxygen when hydrated, and the internal zone is formulated to release the at least one agrochemical into the external zone over a period of at least about one week when the external zone is hydrated.

2. The bead of claim 1, wherein the SAP is capable of absorbing at least about 50 times its weight in water.

3. The bead of claim 1, wherein the SAP is an aerogel, a hydrogel or an organogel.

4. The bead of claim 1, wherein the SAP is a hydrogel.

5. The bead of claim 4, wherein roots of a crop plant are capable of growing within the hydrogel when the hydrogel is hydrated.

6. The bead of claim 4, wherein the hydrogel is capable of repeated swelling cycles that each comprises hydration followed by dehydration.

7. The bead of claim 1, wherein the external zone does not contain the at least one agrochemical before the bead is hydrated for the first time.

8. The bead of claim 1, having a maximum diameter of about 1, 2, 3, 4, 5, 6, 7, 8, 9, or 10 cm when the SAP of the external zone is about 5%, 10%, 15%, 20%, 25%, 30%, 35%, 40%, 45%, 50%, or 5-50% hydrated.

9. The bead of claim 4, wherein the hydrogel is a synthetic hydrogel, a natural carbohydrate hydrogel, or a pectin or protein hydrogel, or any combination thereof.

10. The bead of claim 9, wherein the synthetic hydrogel comprises acrylamide, an acrylic derivative, or any combination thereof.

11. The bead of claim 4, wherein the hydrogel comprises a natural super absorbent polymer (SAP), a poly-sugar SAP, a semi-synthetic SAP, a fully-synthetic SAP, or any combination thereof.

12. The bead of claim 1, wherein the internal zone comprises an organic polymer, a natural polymer, or an inorganic polymer, or any combination thereof.

13. The bead of claim 1, wherein the at least one core is coated with at least one coat compound.

14. The bead of claim 1, wherein the core comprises at least about 0.1 grams of the at least one agrochemical.

15. The bead of claim 1, wherein the at least one agrochemical is:
   i) at least one fertilizer compound;
   ii) at least one pesticide compound,
   iii) at least one hormone compound;
   iv) at least one drug compound;
   v) at least one chemical growth agents; and/or
   vi) at least one microelement.

16. The bead of claim 1, wherein the at least one agrochemical is at least one fertilizer compound.

17. The bead of claim 1, wherein the at least one agrochemical is released from the core of the internal zone over a period of at least about one week when the SAP of the external zone is hydrated.

18. A method of growing a plant, comprising adding at least one bead of claim 1 to the medium in which the plant is grown.

19. A method of growing a plant, comprising adding multiple beads of claim 1 to the medium of the plant, wherein the multiple beads comprise three fertilizer compounds, such that the total N, P, and K content as $(NH_4)_2SO_2$, $NH_4H_2PO_4$, and $KCl$ in the medium as part of the beads is about 25, 5, and 30 g/m$^2$, respectively.

20. A method of generating an artificial zone with predetermined chemical properties within the root zone of a plant, comprising:
   i) adding at least two different beads to the root zone of the plant; or
   ii) adding at least two different beads to the anticipated root zone of the medium in which the plant is anticipated to grow,
   wherein at least one of the at least two different beads is as defined in claim 1.

* * * * *